US009265951B2

(12) United States Patent
Sweeney

(10) Patent No.: US 9,265,951 B2
(45) Date of Patent: Feb. 23, 2016

(54) SYSTEM AND METHOD FOR AUTOMATED ADJUSTMENT OF CARDIAC RESYNCHRONIZATION THERAPY CONTROL PARAMETERS

(75) Inventor: Michael O. Sweeney, Newton, MA (US)

(73) Assignee: THE BRIGHAM AND WOMEN'S HOSPITAL, Boston, MA (US)

(*) Notice: Subject to any disclaimer, the term of this patent is extended or adjusted under 35 U.S.C. 154(b) by 18 days.

(21) Appl. No.: 13/577,968

(22) PCT Filed: Jul. 16, 2010

(86) PCT No.: PCT/US2010/042337
§ 371 (c)(1),
(2), (4) Date: Aug. 9, 2012

(87) PCT Pub. No.: WO2011/099992
PCT Pub. Date: Aug. 18, 2011

(65) Prior Publication Data
US 2012/0310297 A1  Dec. 6, 2012

Related U.S. Application Data

(60) Provisional application No. 61/337,817, filed on Feb. 12, 2010, provisional application No. 61/345,251, filed on May 17, 2010, provisional application No. 61/357,617, filed on Jun. 23, 2010, provisional application No. 61/362,972, filed on Jul. 9, 2010.

(51) Int. Cl.
*A61N 1/362* (2006.01)
*A61N 1/368* (2006.01)
*A61B 5/0452* (2006.01)

(52) U.S. Cl.
CPC .......... *A61N 1/3627* (2013.01); *A61B 5/04525* (2013.01); *A61N 1/368* (2013.01); *A61N 1/3684* (2013.01)

(58) Field of Classification Search
CPC .. A61B 5/04525; A61B 5/7264; A61N 1/368; A61N 1/3627; A61N 1/3682; A61N 1/365; A61N 1/36117; A61N 1/3684
USPC .............................. 607/14, 17–18, 25, 27–28
See application file for complete search history.

(56) References Cited

U.S. PATENT DOCUMENTS 4,233,987 A   11/1980  Feingold
4,428,378 A    1/1984  Anderson et al.
(Continued)

FOREIGN PATENT DOCUMENTS

EP   1 072 284 A2   1/2001
EP   1 504 713 A1   2/2005
(Continued)

OTHER PUBLICATIONS

International Search Report and Written Opinion under date of mailing of Mar. 31, 2011 in connection with PCT/US2010/042337.
(Continued)

*Primary Examiner* — Catherine Voorhees
(74) *Attorney, Agent, or Firm* — Quarles & Brady, LLP

(57) ABSTRACT

A system and method for cardiac resynchronization therapy in which pacing control parameters are automatically adjusted by comparison of local electrograms acquired by a cardiac implantable electrical device with a model of cardiac electrical activity derived from surface-lead electrocardiograph measurements under baseline and paced conditions is provided. The adjusted pacing control parameters guarantee substantially maximum evidence of ventricular activation wavefront fusion while reducing the risk of compromising diastolic function. Atrioventricular intervals (AVIs] are measured and utilized to constrain the adjustment of pacing control parameters such that diastolic dysfunctions are not induced in the patient's heart.

19 Claims, 14 Drawing Sheets

(56) References Cited

U.S. PATENT DOCUMENTS

| | | |
|---|---|---|
| 4,497,326 A | 2/1985 | Curry |
| 4,674,511 A | 6/1987 | Cartmell |
| 5,052,388 A | 10/1991 | Sivula et al. |
| 5,054,496 A | 10/1991 | Wen et al. |
| 5,311,873 A | 5/1994 | Savard et al. |
| 5,443,492 A | 8/1995 | Stokes et al. |
| 5,628,778 A | 5/1997 | Kruse et al. |
| 5,671,752 A | 9/1997 | Sinderby et al. |
| 5,810,740 A | 9/1998 | Paisner |
| 5,891,045 A | 4/1999 | Albrecht et al. |
| 5,922,014 A | 7/1999 | Warman et al. |
| 6,055,448 A | 4/2000 | Anderson et al. |
| 6,187,032 B1 | 2/2001 | Ohyu et al. |
| 6,236,883 B1 | 5/2001 | Ciaccio et al. |
| 6,311,089 B1 | 10/2001 | Mann et al. |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,473,638 B2 | 10/2002 | Ferek-Petric |
| 6,480,745 B2 | 11/2002 | Nelson et al. |
| 6,507,756 B1 | 1/2003 | Heynen et al. |
| 6,584,343 B1 | 6/2003 | Ransbury et al. |
| 6,599,250 B2 | 7/2003 | Webb et al. |
| 6,640,136 B1 | 10/2003 | Helland et al. |
| 6,772,004 B2 | 8/2004 | Rudy |
| 6,804,555 B2 | 10/2004 | Warkentin |
| 6,856,830 B2 | 2/2005 | He |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,092,759 B2 | 8/2006 | Nehls et al. |
| 7,142,922 B2 | 11/2006 | Spinelli et al. |
| 7,215,998 B2 | 5/2007 | Wesselink et al. |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 8,010,194 B2 | 8/2011 | Muller |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,180,428 B2 | 5/2012 | Kaiser et al. |
| 8,195,292 B2 | 6/2012 | Rosenberg et al. |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,401,616 B2 | 3/2013 | Verard et al. |
| 8,478,388 B2 | 7/2013 | Nguyen et al. |
| 8,527,051 B1 | 9/2013 | Hedberg et al. |
| 8,583,230 B2 | 11/2013 | Ryu et al. |
| 8,617,082 B2 | 12/2013 | Zhang et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 2002/0161307 A1 | 10/2002 | Yu et al. |
| 2004/0015081 A1* | 1/2004 | Kramer et al. ............... 600/439 |
| 2004/0059237 A1 | 3/2004 | Narayan et al. |
| 2004/0097806 A1 | 5/2004 | Hunter et al. |
| 2004/0122479 A1 | 6/2004 | Spinelli et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215252 A1 | 10/2004 | Verbeek et al. |
| 2004/0220635 A1 | 11/2004 | Burnes |
| 2004/0267321 A1* | 12/2004 | Boileau et al. ............... 607/3 |
| 2005/0008210 A1 | 1/2005 | Evron et al. |
| 2005/0027320 A1 | 2/2005 | Nehls et al. |
| 2005/0096522 A1 | 5/2005 | Reddy et al. |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0253162 A1 | 11/2006 | Zhang et al. |
| 2007/0142871 A1 | 6/2007 | Libbus et al. |
| 2007/0250129 A1 | 10/2007 | Van Oort |
| 2007/0265508 A1* | 11/2007 | Sheikhzadeh-Nadjar et al. ............... 600/300 |
| 2008/0021336 A1 | 1/2008 | Dobak |
| 2008/0058656 A1 | 3/2008 | Costello et al. |
| 2008/0119903 A1* | 5/2008 | Arcot-Krishnamurthy et al. ............... 607/17 |
| 2008/0140143 A1* | 6/2008 | Ettori et al. ............... 607/14 |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099619 A1 | 4/2009 | Lessmeier et al. |
| 2009/0112109 A1 | 4/2009 | Kuklik et al. |
| 2009/0143838 A1* | 6/2009 | Libbus et al. ............... 607/44 |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |

(56) References Cited

U.S. PATENT DOCUMENTS

| | | |
|---|---|---|
| 2010/0049063 A1 | 2/2010 | Dobak, III |
| 2010/0069987 A1 | 3/2010 | Min et al. |
| 2010/0113954 A1 | 5/2010 | Zhou |
| 2010/0114229 A1 | 5/2010 | Chinchoy |
| 2010/0174137 A1 | 7/2010 | Shim |
| 2010/0198292 A1 | 8/2010 | Honeck et al. |
| 2010/0228138 A1 | 9/2010 | Chen |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054560 A1 | 3/2011 | Rosenberg et al. |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0304407 A1 | 11/2013 | George et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0236252 A1 | 8/2014 | Ghosh et al. |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032172 A1 | 1/2015 | Ghosh |
| 2015/0032173 A1 | 1/2015 | Ghosh |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0265840 A1 | 9/2015 | Ghosh et al. |

FOREIGN PATENT DOCUMENTS

| | | |
|---|---|---|
| EP | 2 016 976 A1 | 1/2009 |
| EP | 2 391 270 A1 | 12/2011 |
| EP | 2 436 309 A2 | 4/2012 |
| EP | 2 435 132 B1 | 8/2013 |
| WO | WO 9826712 A1 | 6/1998 |
| WO | WO 0045700 | 8/2000 |
| WO | WO 0167950 A1 | 9/2001 |
| WO | WO 2005056108 A2 | 6/2005 |
| WO | WO 2006105474 A2 | 10/2006 |
| WO | WO 2006115777 A1 | 11/2006 |
| WO | WO 2006117773 A1 | 11/2006 |
| WO | WO 2007013994 A2 | 2/2007 |
| WO | WO 2007139456 A1 | 12/2007 |
| WO | WO 2008151077 A2 | 12/2008 |
| WO | WO 2009079344 A1 | 6/2009 |
| WO | WO 2009139911 A2 | 11/2009 |
| WO | WO 2009148429 A1 | 12/2009 |
| WO | WO 2010019494 A1 | 2/2010 |
| WO | WO 2010071520 A1 | 6/2010 |
| WO | WO 2010088040 A1 | 8/2010 |
| WO | WO 2010088485 A1 | 8/2010 |
| WO | WO 2011070166 A1 | 6/2011 |
| WO | WO 2011090622 A1 | 7/2011 |
| WO | WO 2012037471 A2 | 3/2012 |
| WO | WO 2012109618 A2 | 8/2012 |
| WO | WO 2012110940 A1 | 8/2012 |
| WO | WO 2012151364 A1 | 11/2012 |
| WO | WO 2012151389 A1 | 11/2012 |
| WO | WO 2013006724 A2 | 1/2013 |
| WO | WO 2013010184 A1 | 1/2013 |
| WO | WO 2014179454 A1 | 11/2014 |
| WO | WO 2014179459 A2 | 11/2014 |
| WO | WO 2015013271 A1 | 1/2015 |
| WO | WO 2015013493 A1 | 1/2015 |
| WO | WO 2015013574 A1 | 1/2015 |

OTHER PUBLICATIONS

Sweeney, et al., Analysis of Ventricular Activation Using Surface Electrocardiography to Predict Left Ventricular Reverse Volumetric Remodeling During Cardiac Resynchronization Therapy, Circulation, 2010, 121:626-634.

PCT International Search Report and Written Opinion, PCT/US2012/023256, Aug. 27, 2012.

PCT International Search Report and Written Opinion, PCT/US2012/046907, Oct. 18, 2012.

International Search Report and Written Opinion issued Sep. 3, 2012 for International Application No. PCTUS2012036262; 9 pages.

International Search Report and Written Opinion issued Sep. 3, 2012 for International Application No. PCTUS2012036302; 9 pages.

International Search Report and Written Opinion issued Aug. 6, 2014 for International Application No. PCTUS2014036153; 14 pages.

International Search Report and Written Opinion issued Nov. 7, 2014 for International Application No. PCTUS2014036163; 12 pages.

International Search Report and Written Opinion issued Oct. 28, 2014 for International Application No. PCTUS2014041928; 15 pages.

International Search Report and Written Opinion issued Oct. 24, 2014 for International Application No. PCTUS2014041929; 14 pages.

International Search Report and Written Opinion issued on Nov. 4, 2014 for International Application no. PCTUS20140247583; 7 pages.

International Search Report and Written Opinion issued on Nov. 12, 2014 for International Application No. PCTUS2014047971; 7 pages.

International Search Report and Written Opinion issued on Nov. 12, 2014 for International Application No. PCTUS2014048120; 7 pages.

International Search Report and Written Opinion issued on Mar. 9, 2015 for International Application No. PCTUS2014069214; 11 pages.

International Search Report and Written Opinion issued on Mar. 17, 2015, for International Application No. PCTUS2014069192; 11 pages.

International Search Report and Written Opinion issued on Mar. 16, 2015 for International Application No. PCTUS2014069182; 11 pages.

International Search Report and Written Opinion issued on Apr. 8, 2015 for International Application No. PCTUS2014069070; 12 pages.

(56) References Cited

OTHER PUBLICATIONS

International Search Report and Written Opinion issued on Jun. 11, 2015 for International Application No. PCTUS2015021442; 13 pages.
Biffi et al., "Occurrence of Phrenic Nerve Stimulation in Cardiac Resynchronization Therapy Patients: the Role of Left Ventricular Lead Type and Placement Site," Europace, 2013; 15:77-82.
"CardioGuide System Enables Real-Time Navigation of Left Ventricular Leads During Medtronic CRT Implants," Press Release, Apr. 9, 2013, Medtronic, Inc., 2 pgs.
Cuculich, P.S., et al., "The Electrophysiological Cardiac Ventricular Substrate in Patients After Myocardial Infection" J. Am. Coll. Cardiol. 2011; 58:1893-1902.
Czerwinska et al., "Method of Segmentation of Thorax Organs Images Applied to Modeling the Cardiac Electrical Field," Engineering in Medicine and Biology Society, Proceedings of the 22nd Annual International Conference of the IEEE, vol. 1, 23, Jul. 23, 2000.; pp. 402-405.
Dawoud, F. et al., "Inverse Electrocardiographic Imaging to Assess Electrical Dyssynchrony in Cardiac Resynchronization Therapy Patients," Computing in Cardiology, 2012; 39:993-996.
Freund et al., "A Decision-Theoretic Generalization of Online Learning and an Application to Boosting," Journal of Computer and System Sciences, 1997; 55(1):119-139.
Friedman, "Greedy Function Approximation: A Gradient Boosting Machine," Annals of Statistics, 2001; 29 (5):1189-1232.
Friedman, "Stochastic Gradient Boosting," Computational Statistics and Data Analysis, 2002; 38(4):367-378.
Friedman et al., "Additive Logistic Regression: a Statistical View of Boosting," Annals of Statistics, 2000; 28(2):337-374.
Ghosh et al. "Accuracy of Quadratic Versus Linear Interpolation in Noninvasive Electrocardiographic Imaging (ECGI)," Annuals of Biomedical Engineering, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" Circulation, 2008; 118:907-915. Published online Aug. 12, 2008.
Ghosh et al. "Application of L1-Norm Regularization to Epicardial Potential Solution of the Inverse Electrocardiography Problem," Annuals of Biomedical Engineering, vol. 37, No. 5, May 2009; pp. 902-912.
Gold et al., "Comparison of Stimulation Sites within Left Ventricular Veins on the Acute Hemodynamic Effects of Cardiac Resynchronization Therapy" Heart Rhythm, Apr. 2005; 2(4):376-381.
Gulrajani, "The Forward and Inverse Problems of Electrocardiography," IEEE Engineering in Medicine and Biology, IEEE Service Center, vol. 17, No. 5, Sep. 1, 1988; pp. 84-101, 122.
Hansen, "Regularization Tools: A Matlab Package for Analysis and Solution of Discrete III-Posed Problems," Version 4.1 for Matlab 7.3; Mar., 2008; 128 pages. Retrieved from the Internet: Jun. 19, 2014 http:www.mathworks.commatlabcentralfileexchange52-regtools.
Hayes et al., "Cardiac Resynchronization Therapy and the Relationship of Percent Biventricular Pacing to Symptoms and Survival," Heart Rhythm, Sep. 2011; 8(9):1469-1475.

"Heart Failure Management" datasheet [online]. Medtronic, Minneapolis, Minnesota, [Last updated on Jun. 3, 2013]. Retrieved from the Internet: www.medtronic.com; 9 pages.
Jia et al., "Electrocardiographic Imaging of Cardiac Resynchronization Therapy in Heart Failure: Observation of Variable Electrophysiologic Responses," Heart Rhythm, vol. 3, No. 3; Mar. 1, 2006, pp. 296-310.
Kornreich, et al. "Body Surface Potential Mapping of ST Segment Changes in Acute Myocardial Infarction," Circulation, 1993; 87: 773-782.
Medtronic Vitatron Carelink Encore® Programmer Model 29901 Reference Manual, Copyright 2013 Medtronic, Inc., 21 pages.
Modre et al., "Noninvasive Myocardial Activation Time Imaging: A Novel Inverse Algorithm Applied to Clinical ECG Mapping Data" IEEE Transactions on Biomedical Engineering, vol. 49; No. 10, Oct. 2002; pp. 1153-1161.
Ridgeway, "The State of Boosting," Computing Science and Statistics, 1999; 31:172-181.
Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, Feb. 2010; 21 (2):219-22.
Silva et al., "Cardiac Resynchronization Therapy in Pediatric Congenital Heart Disease: Insights from Noninvasive Electrocardiographic Imaging" Heart Rhythm, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," Circulation, 2011; 123:1159-1166.
Sperzel et al., "Intraoperative Characterization of Interventricular Mechanical Dyssynchrony Using Electroanatomic Mapping System—A Feasibility Study," Journal of Interventional Cardiac Electrophysiology, Nov. 2012; 35 (2):189-196.
Steinhaus BM., "Estimating cardiac transmembrane activation and recovery times from unipolar and bipolar extracellular electrograms: a simulation study," Circulation Research, 1989, 64:449-462.
Turner et al, "Electrical and Mechanical Components of Dyssynchrony in Heart Failure Patients with Normal QRS Duration and Left Bundle-Branch Block," Circulation 2004; 109: 2544-2549.
Van Deursen et al., "Vectorcardiography as a Tool for Wasy Optimization of Cardiac Resynchronization Therapy in Canine LBBB Hearts," Circulation Arrhythmia and Electrophysiology, Jun. 1, 2012; 5(3):544-552. Available online Apr. 24, 2012.
Vardas et al., The Task Force for Cardiac Pacing and Cardiac Resynchronization Therapy of the European Society of Cardiology. Developed in Collaboration with the European Heart Rhythm Association, European Heart Journal, 2007; 28:2256-2295.
Varma et al., "Placebo CRT," Journal of Cardiovascular Electrophysiology, vol. 19, Aug. 2008; p. 878.
Williams et al., "Short-Term Hemodynamic Effects of Cardiac Resynchronization Therapy in Patients With Heart Failure, a Narrow QRS Duration, and No Dyssynchrony," Circulation, Oct. 27, 2009; 120: 1687-1694.

* cited by examiner

SYSTEM AND METHOD FOR AUTOMATED ADJUSTMENT OF CARDIAC RESYNCHRONIZATION THERAPY CONTROL PARAMETERS

CROSS-REFERENCE TO RELATED APPLICATIONS

This application represents the national stage entry of PCT International Application No. PCT/US2010/042337, filed Jul. 16, 2010, which claims the benefit of U.S. Provisional Patent Application Ser. No. 61/337,817, filed on Feb. 12, 2010, and entitled "System And Methods For Automatically Generating Ventricular Activation Wavefront Fusion During Multisite Pacing Therapy"; U.S. Provisional Patent Application Ser. No. 61/345,251, filed on May 17, 2010, and entitled "During Multisite Pacing Therapy, Systems and Methods for Determining Ventricular Activation Times And For Automatically Titrating Maximum Evidence For Ventricular Activation Wavefront Fusion"; U.S. Provisional Patent Application Ser. No. 61/357,617, filed on Jun. 23, 2010, and entitled "A System and Apparatus for Automatically Predicting and Reporting The Probability of Reverse Ventricular Remodeling During Multisite Pacing Therapy"; and U.S. Provisional Patent Application Ser. No. 61/362,972, filed on Jul. 9, 2010, and entitled "Systems, Apparatuses and Methods for Cardiac Resynchronization", all of which are incorporated herein by reference for all purposes.

FIELD OF THE INVENTION

The field of the invention is systems and methods for cardiac rhythm management. More particularly, the invention relates to systems and methods for performing cardiac resynchronization therapy in which adjustments to pacing control parameters are automatically made in relation to a model of cardiac electrical activity, such as a model of global cardiac electrical activity.

BACKGROUND OF THE INVENTION

Left ventricular conduction delay due to bundle branch block causes regional heterogeneity in contraction and stretch, or asynchrony, which reduces pump function and stimulates negative left ventricular remodeling, such as increased chamber volumes. Experimental models have demonstrated a direct linkage between left ventricular electrical activation, cardiac mechanics, and remodeling. The conceptual basis of multisite pacing, which is also referred to as cardiac resynchronization therapy ("CRT") or biventricular pacing, for asynchronous heart failure is to minimize ventricular conduction delay, which reduces contractile asynchrony and improves chamber mechanics. Resynchronization of electromechanical activation induces so-called "reverse" remodeling, characterized by ventricular volume reductions, and improved pump function, characterized by increased ventricular ejection fraction. Reverse remodeling is associated with reduced heart failure morbidity and mortality. However, up to one-third of patients do not improve following CRT.

The translational mechanism for reverse volumetric remodeling in response to multisite pacing for asynchronous heart failure is ventricular activation wavefront fusion, which is evident on the paced 12-lead surface ECG. Presence of ventricular activation wavefront fusion predicts increased probability of reverse remodeling, whereas absence of wavefront fusion predicts reduced probability of remodeling, regardless of baseline substrate conditions.

Unfavorable substrate conditions, such as high myocardial scar volume or small amounts of ventricular conduction delay, cannot be modified by pacing techniques. In contrast, pacing strategies can be readily adapted to modify ventricular activation, and such instructions can be implemented automatically in the fully ambulatory patient having a cardiac implantable electrical device ("CIED"). Recent experimental evidence indicates that only two-thirds of CIED patients have paced surface ECG evidence of ventricular activation wavefront fusion during conventional CRT. This implies that failure to correct ventricular conduction delay, despite conventional CRT pacing, contributes significantly to volumetric remodeling non-response.

The limitation of all existing CIED approaches to automatic or semi-automatic adjustment of pacing control systems for CRT is that they rely solely on limited device-based measurements that have not been correlated with improvement in any clinical outcome measure, most notably, reverse volumetric remodeling. It would therefore be desirable to provide a system and method for cardiac resynchronization therapy that more accurately characterizes global ventricular activation patterns and that results in clinically reliable measurements and changes to pacing control parameters.

SUMMARY OF THE INVENTION

The present invention overcomes the aforementioned drawbacks by providing a system and method for cardiac resynchronization therapy ("CRT") in which a model of cardiac electrical activity, such as a model of global cardiac electrical activity derived from various surface electrocardiograph ("ECG") signals, is utilized to automatically adjust pacing control parameters of a cardiac implantable electrical device ("CIED") by comparing multiple local and far-field electrograms ("EGMs") acquired by the CIED to the model. Such a system and method provides an accurate characterization of global ventricular activation patterns as observed by the CIED, thereby providing a system and method that can more accurately adjust the appropriate pacing control parameters to achieve substantially optimal ventricular activation. It is, therefore, an aspect of the invention to provide a system and method for cardiac resynchronization therapy that utilize a framework, such as a morphological framework, for analyzing local CIED-based measurements of cardiac electrical activity as surrogates for global cardiac electrical activity.

It is an aspect of the invention to provide a method for delivering cardiac resynchronization therapy to a patient's heart with a CIED for cardiac rhythm management ("CRM"). The therapy is continuously and automatically adjusted using a model of cardiac electrical activity, such as a model of global cardiac electrical activity that is derived from baseline and paced surface electrocardiography signals. A morphological framework is utilized to provide direct, comparative analysis between electrograms acquired with the CIED and the model of cardiac electrical activity.

It is another aspect of the invention to provide a method for delivering cardiac resynchronization therapy to a patient's heart with a CIED for CRM. Pacing control and timing parameters used to direct the therapy are continuously and automatically adjusted using a model of cardiac electrical activity, such as a model of global cardiac electrical activity that is derived from baseline and paced surface electrocardiography signals. Exemplary timing parameters include atrioventricular intervals ("AVIs"), such as intrinsic AVIs ("iAVI"), pacemaker AVIs ("pAVI"), and effective AVIs ("eAVI").

It is yet another aspect of the invention to provide a method for accurately predicting a probability of reverse volumetric ventricular remodeling resulting from a given cardiac resynchronization therapy plan.

It is yet another aspect of the invention to provide a method for automatically titrating maximum evidence of ventricular activation fusion during cardiac resynchronization therapy.

It is yet another aspect of the invention to provide a method for automatically increasing atrial sensitivity of a CIED to overcome failure to achieve maximum evidence of ventricular activation wavefront fusion during multisite pacing and to reduce the risk of left ventricular filling abnormalities, such as diastolic dysfunction, without compromising maximal evidence of ventricular activation wavefront fusion.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Conventional cardiac pacing with implanted cardiac rhythm management ("CRM") devices, such as pacemakers and implantable cardioverter-defibrillators ("ICDs") with pacing functionality, involves delivering electrical pacing pulses to a patient's heart via intracardiac electrodes that are in electrical contact with desired portions of the heart. The CRM device is usually implanted subcutaneously on the patient's chest.

Figure 1:
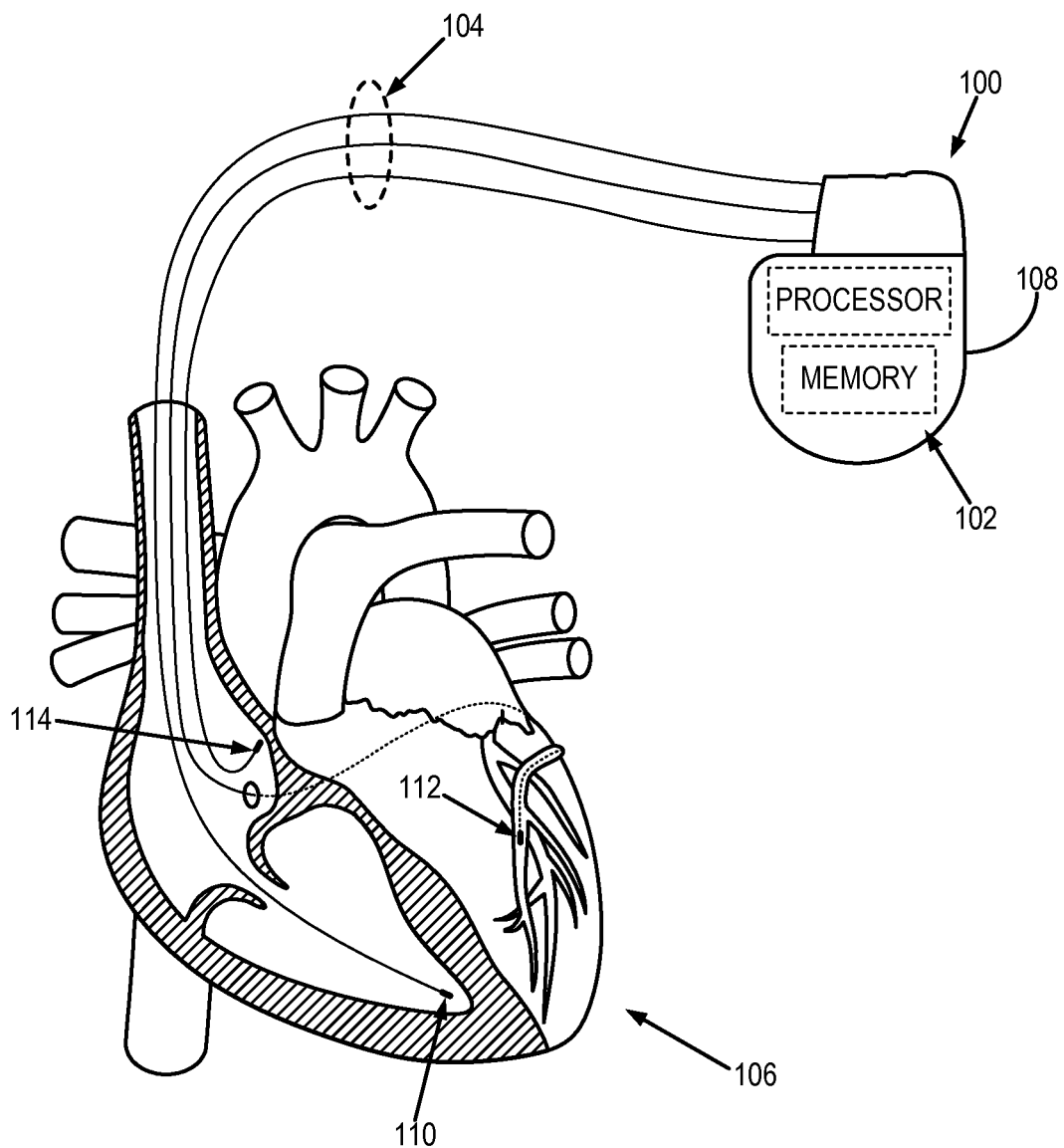
FIG. 1 is a pictorial representation of an exemplary cardiac implantable electronic device ("CIED") for cardiac rhythm management ("CRM") employed when practicing embodiments of the present invention.

Referring now to FIG. 1, an exemplary cardiac implantable electrical device ("CIED") 100 utilized for cardiac resynchronization therapy ("CRT") is illustrated. Such an exemplary CIED 100 includes an implantable pulse generator 102 that is in electrical communication with an intracardiac lead system 104.

Portions of the intracardiac lead system 104 may be inserted into the patient's heart 106 by way of the vessels of the upper venous system, such as the superior vena cava. The intracardiac lead system 104 includes one or more electrodes configured to produce an electrogram ("EGM") signal representing cardiac electrical activity sensed at the location of the electrode, between spatially separated electrodes, or between various combinations of electrodes and a housing 108 of the pulse generator 102, or to deliver pacing electrical pulses to the location of the electrode. Optionally, the intracardiac lead system 104 may include one or more electrodes configured to sense physiological parameters, such as cardiac chamber pressure or temperature.

The lead system 104 may include one or more intracardiac electrodes 110-114 positioned in, on, or about one or more heart chambers for sensing electrical signals from the patient's heart 106 and delivering pacing pulses to the heart 106. The intracardiac electrodes 110-114, such as those illustrated in FIG. 1, may be used to sense electrical activity in or pace one or more chambers of the heart, including the left ventricle, the right ventricle, the left atrium, and the right atrium. The lead system 104 may include one or more defibrillation electrodes for delivering cardioversion/defibrillation electrical shocks to the heart.

The pulse generator 102 includes circuitry for detecting cardiac arrhythmias and controlling pacing or defibrillation therapy in the form of electrical stimulation pulses or shocks delivered to the heart 106 through the lead system 104. The housing 108 of the pulse generator 102 also serves as a sensing electrode for recording far-field EGMs in combination with various selectable intracardiac electrodes 110-114. Such a controller is formed of a microprocessor in electrical communication with a memory for program and data storage. Other controller designs will be readily appreciated by those skilled in the art.

The controller is configured to operate the CRM device 100 in a number of programmed modes, each programmed mode defining how pacing pulses are output in response to sensed cardiac electrical activity or in the absence of spontaneous cardiac electrical activity. Communications circuitry is also provided for facilitating communication between the controller and an external communication device, such as, for example, a portable or bed-side communication station, patient-carried/worn communication station, or external programmer. The communications circuitry may also facilitate unidirectional or bidirectional communication with one or more implanted; external; cutaneous or subcutaneous physiologic or non-physiologic sensors; patient-input devices; or information systems.

The controller controls the overall operation of the CRM 100 device in accordance with programmed instructions stored in memory. The controller interprets electrogram signals sensed from the intracardiac electrodes 110-114, and far-field electrodes formed with the housing 108 of the pulse generator 102, and controls the delivery of pacing electrical pulses in accordance with a programmed pacing mode. The sensing circuitry of the CRM device generates multiple atrial, ventricular, and far-field electrogram signals, alone and in various combinations, from the voltages sensed by the electrodes of a particular channel. An electrogram is analogous to a surface ECG and indicates the time course and amplitude of cardiac depolarization that occurs during either an intrinsic or paced beat.

A morphological framework is developed to provide direct, comparative analysis of electrograms ("EGMs") acquired with a CIED and electrocardiograms acquired with an electrocardiograph ("ECG") device employing a surface-lead system. Particularly, a model of cardiac electrical activity is formed from ECGs acquired before and after pacing with a CRM device. Thus, this model conveys information pertaining to abnormal baseline global cardiac electrical activity, changes in global cardiac electrical activity effectuated by a CRM device, and desirable global cardiac electrical activity that maximizes ventricular activation wavefront fusion, thereby guaranteeing maximum odds of improvement in cardiac pump function. While the EGMs do not share the same point-of-view as the surface-lead system commonly employed by an ECG device to record global cardiac activity, by way of the morphological framework, the model of cardiac electrical activity is directly compared to EGMs recorded by a CIED. Therefore, multiple CIED EGMs function as morphologic surrogates for surface ECG measures of global cardiac electrical activity.

Figure 2:
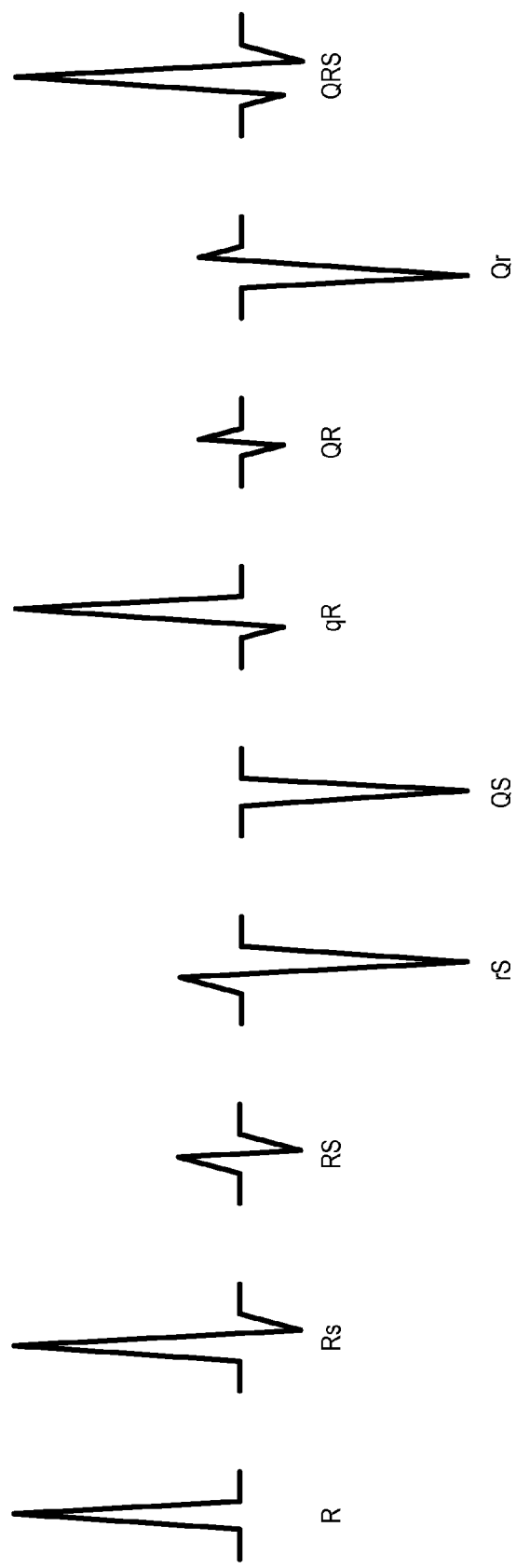
FIG. 2 is a pictorial illustration of a set of exemplary QRS complex hieroglyphs, or "glyphs," that form a morphological framework for correlating CIED measurements of cardiac electrical activity with surface ECG measurements of global cardiac electrical activity shown to predict improvement in ventricular pump function (reverse remodeling)

The morphological framework is referred to as a QRS hieroglyphic framework for ventricular activation pattern comparisons. Briefly, the pre-pacing and post-pacing QRS complex in each surface lead is deconstructed into four possible waveform elements: R, S, Q, and QS. Absolute amplitudes in millivolts ("mV") and durations in milliseconds ("ms") of all elements of each QRS complex are used to characterize specific activation patterns. Ventricular activation in each surface lead can be characterized by nine possible patterns, or QRS hieroglyphs ("glyphs"), as described below in Table 1 and illustrated in FIG. 2.

TABLE 1

| Glyph | Description |
|---|---|
| R | Only R-wave present |
| RS | R-wave and S-wave present with equal amplitude |
| Rs | R-wave and S-wave present, R-wave with greater amplitude |
| rS | R-wave and S-wave present, S-wave with greater amplitude |
| QS | Q-wave and S-wave present with equal amplitude |
| qR | Q-wave and R-wave present, R-wave with greater amplitude |
| QR | Q-wave and R-wave present with equal amplitude |
| Qr | Q-wave and R-wave present, Q-wave with greater amplitude |
| QRS | Q-wave, R-wave, and S-wave are all present |

Typical ventricular activation during left bundle branch block ("BBB") is registered as right-to-left in the frontal plane, anterior-to-posterior in the horizontal plane, and variable axis on the surface ECG. By way of example for characterizing cardiac electrical activity recorded with surface leads in the QRS hieroglyph framework, this ventricular conduction block produces a stereotypic hieroglyphic signature with dominant positive forces in surface leads I, aVL (glyphs: R, Rs), negative forces in aVR (glyph: QS), variable forces in II, III, AVF (glyphs: R, Rs, rS, QS), dominant negative forces in V1-V2 (glyphs: QS, rS), transition in V3-V5 (glyphs: rS into Rs, R) and dominant positive forces in V5-V6 (glyphs: R, Rs). Other characteristic QRS hieroglyphic signatures can be similarly constructed for different forms of ventricular conduction block.

Experimental models of left BBB demonstrate that maximum improvement in ventricular pump function occurs when intra-left ventricle electrical asynchrony is minimized by ventricular activation wavefront fusion. Wavefront opposition and reversal during multisite pacing yields predictable ECG-evidence of ventricular activation wavefront fusion as follows. First, changes in frontal plane electrical axis result in normal or left axis deviation ("LADEV") changing to right axis deviation ("RADEV"). This deviation indicates reversal of activation in the frontal plane, such as, from right-to-left to left-to-right. Similarly, activation reversal in the horizontal plane is indicated by a change in dominant electrical forces from anterior-to-posterior to posterior-to-anterior. Such representative directional changes in global ventricular electrical activation are correlated, but may be manifest in differing degrees depending upon interactions between baseline electrical activation, paced activation, pacing control parameters, pacing lead position, and other considerations. An alternate way of characterizing evidence of ventricular fusion is to use regional or global measures of changes in maximum R-wave amplitude in the expected direction indicating activation wavefront reversal before and after pacing. This method will be described in further detail later.

In addition, changes in QRS hieroglyphic signatures become apparent as rightward forces emerge in leads with dominant leftward forces. For example, qR, QR, and QS glyphs replace R, Rs, or RS glyphs in leads I and aVL. These changes indicate reversal of activation in the frontal plane, such as, from right-to-left to left-to-right. Additionally, anterior forces emerge in leads with dominant posterior forces, as characterized by the change of the QS glyph in lead V1 to the rS, RS, Rs, or R glyph; the change of the QS or rS glyph in lead V2 to the RS, Rs, or R glyph; the change of the rS or RS glyph in V3 to the Rs or R glyph; and so on. These changes indicate reversal of activation in the horizontal plane, such as, from anterior-to-posterior to posterior-to-anterior. The foregoing information pertaining to baseline surface lead measurements of global cardiac electrical activity and expected changes in those measurements during multisite pacing, translated into the QRS hieroglyph framework, is incorporated into a model of cardiac electrical activity that can be interpreted by a CIED and compared to EGMs recorded therewith.

It is noted that the expected changes in local and regional QRS hieroglyphic signatures are most pronounced in specific surface ECG leads: I, aVL, V1, and V2, which are hereby designated as "pivotal leads." These pivotal leads characterize global ventricular activation in the perpendicular frontal and horizontal planes. Leads I and aVL indicate global activation in the right-to-left direction in the frontal plane, while leads V1 and V2 indicate global activation in the anterior-to-posterior direction in the horizontal plane. Therefore, an alternate approach to analysis of global ventricular activation utilizes a cardiac electrical activity model with information from a reduced surface ECG lead set without compromising accuracy.

An exemplary reduced lead set includes 1-2 leads for evaluating activation wavefront reversal in the frontal plane (e.g., I, aVL leads) and 1-2 leads in the horizontal plane (e.g., V1, V2 leads). Additionally, an even simpler surface ECG lead set including only pivotal leads I and V1 could alternatively provide sufficient observational power for detecting activation wavefront reversal in the frontal and horizontal planes.

The herein described method for cardiac resynchronization therapy delivery performed in accordance with some embodiments of the invention is broadly summarized in two stages. First, a model of cardiac electrical activity is produced and provided to a CRM device and, second, EGMs recorded by the CRM device are compared with the provided model in real-time so that pacing control parameters are continuously adjusted to provide substantially optimal global ventricular activation wavefront fusion on a continuous, beat-to-beat, or nearly continuous basis. The model of cardiac electrical activity is produced by first acquiring ECG signals from surface leads before and after pacing. These signals are then analyzed for global ventricular activation. Using the QRS hieroglyph framework, markers of global ventricular activation wavefront fusion in the acquired ECG signals are transferred to CIED EGM surrogates for the surface ECG measurements. Such surrogates are formed of single or multiple, complementary intracardiac, local and far-field EGM QRS glyphs.

Figure 3:
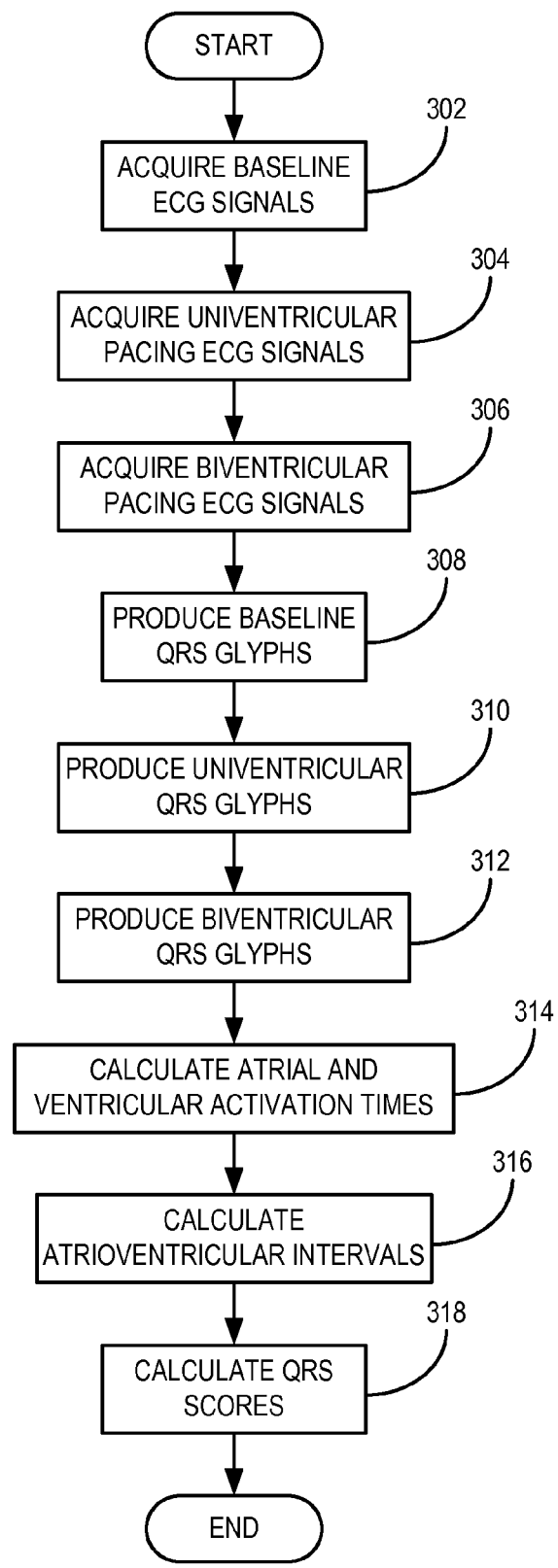
FIG. 3 is a flow chart setting forth the steps of an exemplary method for acquiring and producing data that forms a model of global cardiac electrical activity employed when practicing the present invention.

Referring now to FIG. 3, a flow chart setting forth the steps of an exemplary method for producing a model of cardiac electrical activity, such as a model of global cardiac electrical activity, from surface ECG measurements is illustrated. It is contemplated that a patient-specific model will be produced following implantation of a CIED; however, in the alternative a "standard" model produced in accordance with this method can be preloaded onto individual CRM devices.

To produce a model of cardiac electrical activity, baseline ventricular activation is first evaluated in the complete absence of ventricular pacing, as indicated at step 302. If a model of cardiac electrical activity is produced from a patient who already has an implanted CRM device, this baseline condition is achieved by switching the CRM device into a selectable temporary test mode such as one of the ODO, OVO, or VVI modes. For patients with no spontaneous ventricular electrical activity, baseline ventricular activation is evaluated during right ventricular pacing, which is a physiologic surrogate for left bundle branch block.

Paced univentricular (monochamber) activation sequences are then analyzed, as indicated at step 304. This analysis requires full replacement of native ventricular activation with paced activation. Several means of achieving fully paced univentricular activation are known to those skilled in the art, as a matter of operator preference. For example, right univentricular ("RUV") pacing and left univentricular ("LUV") pacing are performed in a temporary test mode such as the VVI mode. Here, pacing is programmed at a rate that exceeds the prevailing ventricular rate by at least ten beats per minute ("bpm"), thereby eliminating fusion with native contralateral ventricular activation. Alternately, paced global activation, rather than monochamber ventricular activation, may be assessed in the single chamber mode, such as the VVI mode, as described above, or in the dual chamber mode, such as the DDD mode, by selecting a pacemaker atrioventricular interval ("pAVI") that is at least fifty percent of the native AVI during spontaneous atrioventricular conduction.

Simultaneous biventricular pacing, the typical primary therapy mode, is initiated and the resulting signals recorded, as indicated at step 306. In the dual chamber mode, the pAVI should be sufficiently short to guarantee complete replacement of native ventricular activation with paced ventricular activation. In the single chamber ventricular-only mode, the lower rate should exceed the prevailing native ventricular rate by a sufficient amount to eliminate the possibility of fusion with native activation, such as 10-20 bpm above the prevailing rate. Simultaneous paced biventricular activation is analyzed with the real-time surface ECG.

Digital templates of QRS hieroglyphs derived from the surface ECG during spontaneous ventricular activation, or right ventricular paced activation in pacemaker dependent patients, are acquired and stored, as indicated at step 308. Similarly, digital templates for surface ECG hieroglyphs of pivotal leads during univentricular paced ventricular activation, including RUV and LUV, and biventricular ("Bv") paced ventricular activation are acquired and stored, as indicated at steps 310 and 312, respectively. Hieroglyphs for all twelve surface leads are initially acquired. These templates can be displayed on a user interface for comparison during various pacing conditions. Alternately, a reduced surface ECG lead set that includes only 2-4 pivotal leads representing ventricular activation in two perpendicular planes is displayed.

Digital templates of paced QRS hieroglyphs for all twelve surface leads, or for a reduced lead set using 2-4 pivotal leads, are acquired during simultaneous BV paced activation. These hieroglyphs are presented side-by-side with the corresponding QRS hieroglyphs acquired during baseline ventricular activation. A comparison is made for evidence of ventricular activation wavefront fusion on the basis of pacing-induced changes in QRS hieroglyphic signatures. Several comparison approaches are possible and include direct side-by-side visual comparison and semi-automatic or fully automatic template overlapping comparison using mathematical techniques known to those skilled in the art.

If the simultaneous biventricular pacing does not provide maximal evidence of ventricular activation wavefront fusion, manual, semi-automatic, or fully automatic adjustments to ventricular pace timing control parameters are made. The QRS hieroglyphic template acquisition and comparison process is repeated until maximum evidence of fusion is generated. Exemplary control parameter adjustments include manipulation of the pAVI, such as by shortening; or more likely, sequentially timed BV pacing timing, such as V-V timing. For V-V timing, the electrically delayed ventricle is stimulated at fixed or variable intervals prior to the early activated ventricle until maximal evidence of fusion is generated. Such adjustments, and others of a related nature, are well known to those skilled in the art.

Upon achieving maximal evidence of paced activation wavefront fusion using QRS hieroglyphic template analysis, digital templates of paced QRS hieroglyphs for all twelve leads, or for a reduced lead set using 2-4 pivotal leads, at the final pacing control parameter settings may be acquired and stored in the model of cardiac electrical activity. These hieroglyphs can be presented side-by-side with the corresponding QRS hieroglyphs during baseline ventricular activation for real-time or off-time comparison. Further, these hieroglyphs can be used for future manipulations, thereby eliminating the ongoing need for a twelve lead ECG during follow-ups in the clinic.

Digital templates of QRS hieroglyphs derived from the surface ECG during spontaneous ventricular activation, or right ventricular paced activation in pacemaker dependent patients, are acquired and stored. Hieroglyphs for all twelve leads are initially acquired. From the surface ECG measurements, atrial and ventricular activation times can be calculated and stored, as indicated at step 314, and as described below in detail. The QRS hieroglyph templates may be displayed on a user interface for comparison analysis of ventricular activation times ("VATs") by anatomic region. In such an instance, VATs are measured on the external programmer user interface display using electronic calipers. QRS complex duration is also measured, annotated by lead/anatomic region, and automatically stored. Right VAT is measured from QRS onset to the first notch (as described below) in one or more leads by anatomic region. Left VAT is automatically calculated for each right VAT measurement on a running basis until all anatomic regions have been surveyed. The maximum left VAT, $LVAT_{max}$, is then designated as the longest left VAT in any lead from any anatomic region. If spontaneous ventricular activation is absent, VATs are measured during paced right univentricular (monochamber) activation. The process of determining right and left VAT is similarly constructed.

If QRS notching is absent during native ventricular activation or paced right univentricular activation, $LVAT_{max}$ is derived using a regression formula for QRS duration that will be described below in detail. In this situation, the longest QRS duration recorded in any lead by anatomic region is used to calculated $LVAT_{max}$.

As will be described below in detail, atrioventricular interval information can also be calculated and stored in the model of cardiac electrical activity, as indicated at step 316. Similarly, QRS score information (for estimation of scar volume) is calculated from the surface ECG measurements, as indicated at step 318.

An alternate approach to the analysis of global ventricular activation limits the surface ECG measurements to a reduced lead set without compromising accuracy of the resulting model of cardiac electrical activity. This lead set includes 1-2 pivotal leads for evaluating activation wavefront reversal in the frontal plane, such as leads I and aVL, and 1-2 pivotal leads in the horizontal plane, such as leads V1 and V2.

During cardiac resynchronization therapy, these surface ECG markers of regional and global ventricular activation are translated to pivotal CIED QRS EGM sources that display changes in amplitude and directionality of primary or component electrical forces similar to those changes in the pivotal surface ECG leads. The magnitudes of the QRS EGM glyph changes are automatically titrated by adjusting pacing control parameters to yield maximum evidence of activation wavefront reversal. This requires accurate correlations between the surface ECG activation patterns to CRM device-based QRS EGM glyph surrogates that can be exploited for automaticity. Such an analysis utilizes the model of cardiac electrical activity to ensure this accuracy.

Figure 4:
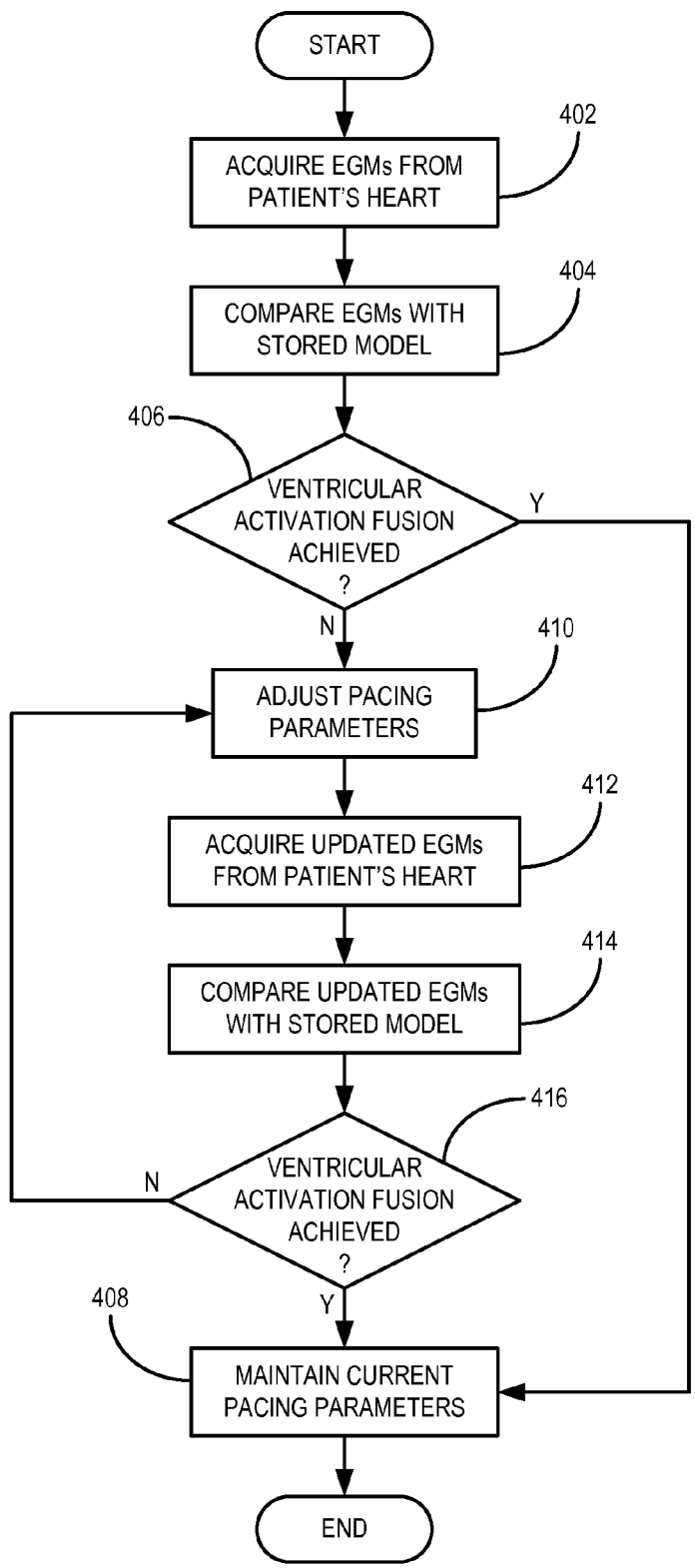
FIG. 4 is a flow chart setting forth the steps of an exemplary method for automatically adjusting cardiac resynchronization therapy pacing control parameters.

Referring particularly now to FIG. 4, a flowchart setting forth the steps of an exemplary method for cardiac resynchronization therapy in which pacing control parameters are continuously and automatically updated based on a model of cardiac electrical activity is illustrated. Such a method begins with the passive acquisition of electrograms ("EGMs") from a patient's heart by a cardiac rhythm management ("CRM") device implanted in the patient, as illustrated at step 402. As illustrated at step 404, the acquired EGMs are then compared with a model of cardiac electrical activity, such as a model of global cardiac electrical activity derived from surface ECG measurements obtained before and during pacing of a patient's heart. As described above, such a model of cardiac electrical activity includes QRS hieroglyphs indicative of, for example, baseline ventricular activation without pacing, univentricular activation, and biventricular activation. The information contained in the model can be acquired with a full twelve-lead surface ECG setup, or alternatively with a reduced lead setup in which measurements are made on only 2-4 pivotal leads.

During the comparison, the candidate EGMs are analyzed in real-time for evidence of changes in amplitude and directionality of major electrical forces, or component forces, in proportion to similar changes in the paced QRS glyphs contained in the model. Neither the absolute proportion nor absolute directionality, such as above or below baseline, is essential for this comparison because the EGMs do not necessarily duplicate the point-of-view of the surface ECG leads used to produce the model. Additionally, the specific deflection component of the EGMs that demonstrate changes in amplitude and directionality proportionate to the changes in paced EGMs is not important; rather, the comparison method searches for a consistent change in the EGMs that is mathematically linked to the desired changes contained in the model of cardiac electrical activity.

The proportionate changes in the model QRS glyphs and acquired EGMs from baseline to maximal ventricular activation fusion are automatically quantified and used as a reproducible numerical endpoint for subsequent titration and maintenance of critical pacing control parameters. For example, indices of change in EGM glyph dominant amplitude or component deflection satisfying the above conditions are generated by calculating the change in dominant amplitude or component deflection for each EGM glyph from baseline to post-pacing, as a proportion of the baseline value. For example, the post-pacing value is used when a deflection of interest is absent at baseline and present post-pacing; a value of one is used where a deflection of interest is present at baseline and absent post-pacing; and a value of zero used where both are absent. Dominant force or component deflection amplitude change values are set to positive if the change is in the expected direction in the model; negative otherwise. These change values are then averaged across EGMs for the individual patient. Several different summaries can then be created, for example, mean change in EGM by region, or mean of all EGMs. By this means, one or more complimentary reproducible numerical endpoints for titration and maintenance of critical pacing control parameters for establishing maximal evidence of ventricular activation wavefront fusion are generated.

Figure 5:
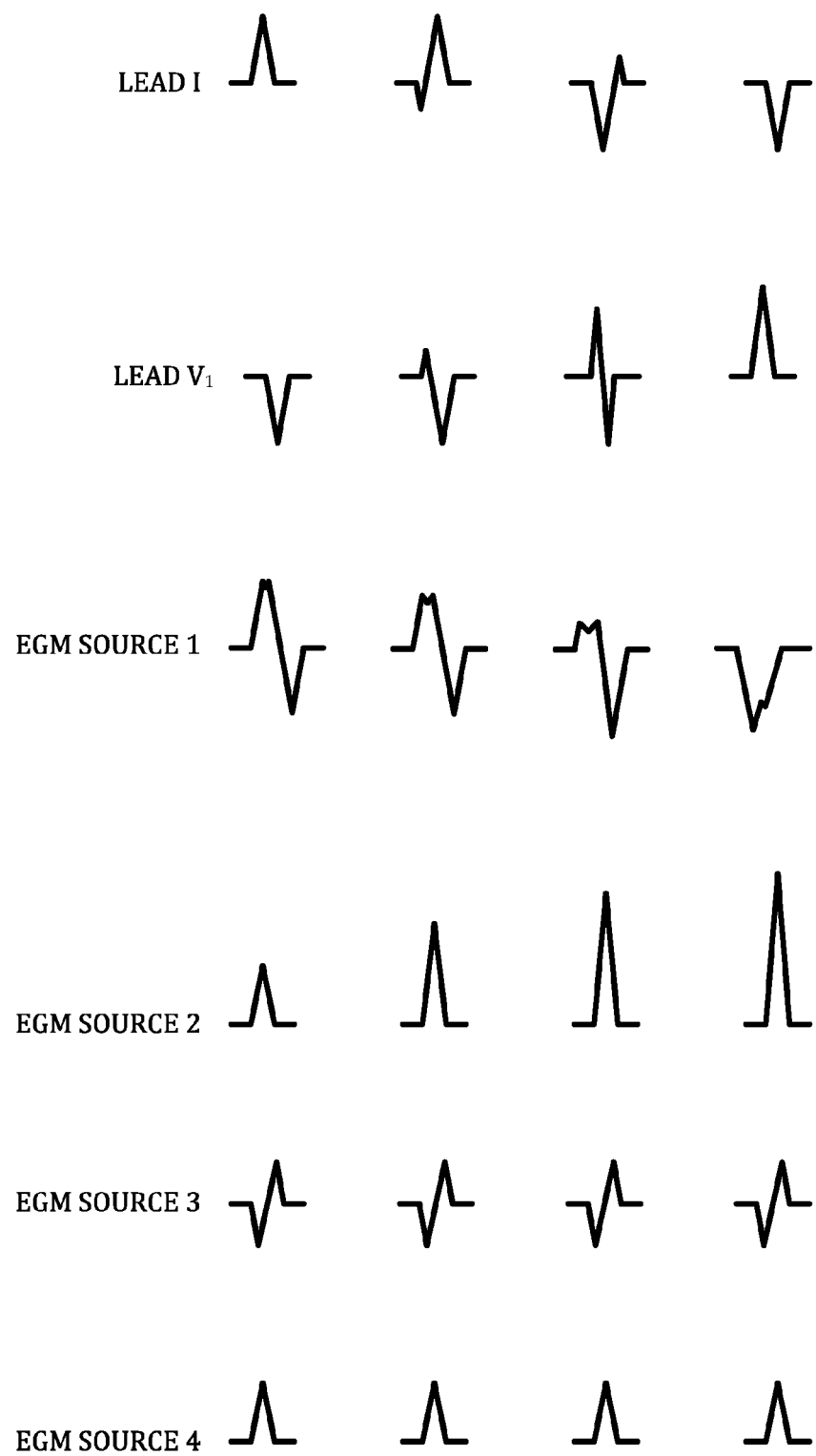
FIG. 5 is a pictorial illustration of a set of exemplary surface electrocardiograph ("ECG") lead measurements and CIED-based electrogram ("EGM") measurements.

Referring now to FIG. 5, an example of a comparison between a model of cardiac electrical activity and EGMs recorded from an implanted CRM device is illustrated. Exemplary ECG signals from surface leads I and V1 representing progressive wavefront reversal and indicating ventricular activation fusion, are shown. Similarly, exemplary QRS glyph EGM morphologies from four sources are shown. A real-time comparison of ventricular activation fusion evidence is performed between the QRS glyphs represented by the EGM signals. The two surface lead measurements in the model of cardiac electrical activity show proportionate changes in dominant amplitude or component deflection during progressive fusion. These are suitable for morphometric and numerical analysis as described above. The latter two QRS glyph EGM morphologies, sources 3 and 4, show insufficient changes despite progressive activation fusion and are therefore rejected for analysis. On the contrary, the first two QRS glyph EGM morphologies, sources 1 and 2, show sufficient and proportionate changes in dominant amplitude or component deflection during progressive fusion and are therefore accurate and reliable evidence of ventricular activation fusion when compared with the model of cardiac electrical activity.

Referring again to FIG. 4, if, after comparison, the determination is made at decision block 406 that the substantially maximal evidence of ventricular activation wavefront fusion is present based on the existing pacing control parameters, the existing parameters are maintained, as indicated at step 408. On the other hand, if the current pacing control parameters are not resulting in the substantially maximal evidence of ventricular activation wavefront fusion, then the titration of this maximum evidence is performed in order to determine more appropriate pacing control parameters.

Thus, as indicated at step 410, the current pacing control parameters are adjusted in order to achieve more appropriate pacing of the patient's heart. Exemplary pacing control parameters include AVI timing, interventricular timing, atrial sensitivity, and pacing stimulus output voltages. Following an adjustment to the pacing control parameters, a new set of EGMs are acquired from the CRM device, as indicated at step 412. These updated EGMs are then compared with the model of cardiac electrical activity in the manner described above, as indicated at step 414. Once again, the results of the comparison are analyzed at decision block 416. If the adjusted pacing control parameters resulted in the titration of maximum evidence of ventricular activation wavefront fusion, then the updated pacing control parameters are maintained, as indicated at step 408. Otherwise, the pacing control parameters are again adjusted at step 410 and steps 412-414 repeated to assess the efficacy of the updated pacing control parameters.

Using this method, one or more unique EGM QRS glyphs demonstrating the dynamic characteristics corresponding to global ventricular activation during maximal evidence of ventricular activation fusion are identified, acquired, and linked to the corresponding titrated pacing control parameters. It is contemplated that a combination of near- and far-field EGM QRS glyphs would be employed. The use of multiple EGM QRS glyphs would increase the reproducibility and accuracy of global ventricular activation imaging for future automatic adjustments.

Pacing control parameters are periodically updated to maintain maximum amplitude and directionality of the dominant amplitude or component deflection of the EGM QRS glyphs indicative of maximum ventricular activation wavefront fusion. When a model of cardiac electrical activity derived from a reduced lead set is employed, the need for digital templates of the full EGM QRS glyphs is eliminated; instead, a single component of these EGMs is focused on during the comparative analysis.

Periodic checks of real-time paced CIED EGM QRS glyphs against baseline paced EGM templates during maximum ventricular activation fusion are made. The purpose of periodic surveillance is to detect a clinically relevant change in baseline ventricular conduction characteristics. Such checks can be automatically scheduled at selectable or default time intervals, or automatically triggered by a change in patient or pacing condition, such as by the emergence of pacemaker dependence. A template matching process or mathematical comparison of dominant amplitude or component deflection is used to compare the ongoing real-time EGM QRS glyph templates with the baseline EGM QRS glyph paced activation fusion templates, as described above.

As described above in detail, when the optimal CIED EGM QRS glyph template is not matched, or if the numerical measures derived from analysis of the dominant amplitude or component deflection changes in the expected direction differ significantly from baseline, selectable or automatic adjustments to pacing control parameters are made to restore the highest possible real-time match with the baseline EGM QRS glyph paced global activation fusion templates. Such adjustments include recalibration of AVI timing, interventricular ("V-V") timing, atrial sensitivity, and pacing stimulus output voltages.

Optionally, certain situations may trigger an alert condition where redetermination of ECG and EGM based measures of ventricular activation fusion is advised. For example, a significant change, such as more than a ten percent increase or decrease, in periodically determined dominant amplitude or component deflection shift, as compared to baseline established during maximal evidence of ventricular activation fusion, may be indicative of a clinically relevant change in baseline ventricular activation time and sequence. Such an observation could automatically trigger a reminder to repeat semi-automatic surface ECG and CIED EGM-based measurements at the next clinical follow-up.

It is contemplated that the determination of CIED EGM glyphs that satisfy the above conditions of reproducible and numerically quantifiable changes in dominant amplitude or component deflection corresponding to evidence of ventricular activation wavefront reversal in the pivotal surface ECG leads will be obtained at the time of CIED multisite pacing therapy initiation using a semi-automated process described below. It is unlikely that redetermination of ECG-based activation fusion evidence will be routinely necessary. The purpose of linking CIED-based EGMs to reproducible changes in ventricular activation on the surface ECG is to eliminate the need of surface ECGs during follow-up appointment, exploit EGMs as surrogates for the surface ECG and assessment of changes in global ventricular activation, and instruct automatic changes in pacing control parameters using EGMs to positively modify global ventricular activation on a continuous basis. As such, this approach is a significant departure from prior applications in this field.

In addition to the foregoing automated method, an implanted CRM device may be initially programmed with input from a clinician. In this semi-automated method, a standard twelve lead ECG is linked to an external programmer for the implanted CRM device and displayed on a user interface. An option of a reduced ECG lead set including around 2-4 pivotal leads in two perpendicular viewing planes is offered to the user for simplification. Any of such surface ECG lead sets is displayed in real-time along with intracardiac and body surface EGM QRS glyphs and telemetry markers using a standard radiotelemetry link with the CRM device. For simplification, 2-4 pivotal leads, representing ventricular activation wavefront directionality in the horizontal and frontal planes, may be displayed in parallel with real-time intracardiac or body surface EGM glyphs for visual and morphometric comparison.

The digital templates of the paced QRS hieroglyphs produced during maximum achievable ventricular activation fusion, as stored in the cardiac electrical activity model, are displayed side-by-side with selectable intracardiac EGMs recorded from the implanted CRM device. Unique morphology templates of one or more intracardiac or body surface EGM QRS glyphs corresponding to global ventricular activation during maximal evidence of ventricular activation fusion are identified, acquired and linked to the corresponding titrated pacing control parameters. It is contemplated that a combination of near- and far-field EGM QRS glyph templates will be employed. The use of multiple EGM QRS glyph templates increases the reproducibility and accuracy of global ventricular activation imaging for future automatic adjustments.

When using the reduced lead set, the digital templates of pivotal paced QRS glyphs (leads V1-V2, I and aVL) are displayed in real-time on the CIED-programmer interface during manipulation of pacing control parameters to achieve maximum ventricular activation fusion. A panel of potential candidate CIED QRS EGMs from multiple recording sources is also displayed side-by-side with the pivotal paced QRS glyphs during this process. The candidate CIED QRS EGMs are examined in real time for visual evidence of change in amplitude and directionality of major electrical forces, or component forces, in proportion to similar changes in the pivotal paced QRS glyphs. Neither the absolute proportion nor absolute directionality (e.g., above or below baseline) is essential, since the CEID EGM QRS glyphs do not necessarily duplicate the point-of-view of the surface ECG leads. Additionally, the specific deflection component of the CIED QRS EGM glyph that demonstrates changes in amplitude and directionality proportionate to the changes in pivotal paced QRS EGM glyphs is not important; rather, the user searches for a consistent change in the CIED QRS EGM glyph that can be visually and mathematically linked to the changes in the pivotal surface ECG leads during generation of maximum activation wavefront fusion.

The EGM QRS glyph templates form a CIED-based reduced lead set and provide an accurate and reliably reproducible surrogate for surface ECG QRS hieroglyphs, which are combined to reproducibly image and characterize global ventricular activation. These EGM QRS glyph templates are used for periodic updating of pacing control parameters and are used to instruct timing of ventricular stimulation in order maintain maximal activation fusion continuously. It is contemplated that the use of EGM QRS glyph templates from multiple recording sources will increase the accuracy of reproducing the precise global ventricular activation sequence with adjustments to pacing control parameters.

Once the initial pacing control parameters have been set by the clinician using this foregoing method, the CIED operates in an automatic mode, making the necessary adjustments to pacing control parameters in order to titrate the maximum evidence of ventricular activation wavefront fusion, as described above in detail.

The foregoing method for automatically or semi-automatically adjusting pacing control parameters in a CIED so that maximum evidence of ventricular activation wavefront fusion is achieved to reduce ventricular asynchrony can be supplemented further based on considerations of atrioventricular interval timing. In such an instance, and as will be described below in detail, the pacing control parameters are further adjusted to maintain an appropriate atrioventricular interval ("AVI") such that diastolic dysfunctions are not introduced as a result of the applied cardiac resynchronization therapy.

Correction of ventricular conduction delay to improve ventricular mechanics and induce reverse volumetric remodeling is the primary target of cardiac resynchronization therapy. However, resynchronization of ventricular electromechanical timing directly influences systolic performance. Because the timing of ventricular stimulation is primarily controlled with the pacemaker AVI ("pAVI"), cardiac resynchronization therapy also has direct effects on AV timing, which influences ventricular loading conditions and diastolic function. Diastolic dysfunction is common in systolic heart failure and contributes to symptoms. Optimal AV resynchronization can therefore reduce diastolic dysfunction and improve symptoms. It is noted that AV optimization for diastolic function is not required for ventricular electromechanical resynchronization and plays no role in reverse volumetric ventricular remodeling. Indeed, reverse volumetric ventricular remodeling can occur even when AV timing is not optimized. Consequently, persistent diastolic dysfunction, despite improvement in left ventricle size and contractility, is an important and frequently unrecognized source of symptoms in patients with asynchronous heart failure treated with cardiac resynchronization therapy.

Existing methods for titrating optimal AV resynchronization during multisite pacing therapy include echocardiographic analysis of left ventricle inflow velocity patterns, CIED-EGM timing analysis derived from invasive hemodynamic monitoring, and real-time hemodynamic monitoring during manipulation of the pAVI. The common goal of these methods is to identify the single pAVI which yields maximum improvement in left ventricular preload and maximum diastolic filling time. To achieve this goal requires that the timing of left atrial contraction to left ventricular contraction is optimized. When left atrial contraction occurs too early relative to left ventricular contraction, late diastolic active filling, identified by the A-wave on echocardiography, fuses with early diastolic passive filling, identified by the E-wave on echocardiography, thereby reducing left ventricle preload. This form of diastolic dysfunction occurs spontaneously during first degree AV block ("AVB"), frequently accompanies left bundle branch block ("LBBB"), and is corrected by the short pAVIs necessary to achieve maximum evidence of ventricular fusion activation.

An insufficiently short pAVI, particularly in the presence of significant first degree AVB with a long PR interval may result in this form of diastolic dysfunction. This situation is commonly referred to as a pAVI that is "too long" relative to the intrinsic AVI ("iAVI"). A different form of diastolic dysfunction is induced when left atrial contraction occurs simultaneously, or immediately after left ventricular contraction. Late diastolic filling, identified by the A-wave on echocardiography, is truncated by mitral valve closure and in the most extreme form results in atrial transport block. This dysfunction reduces left ventricular preload; causes increased left atrial pressure and pulmonary venous flow reversal, yielding a pattern of restrictive diastolic dysfunction; and can trigger counter-physiologic neurohormonal reflexes. This derangement seldom occurs spontaneously; however, these timing abnormalities can be inadvertently induced by a pAVI that is "too short" relative to the iAVI. Since early passive filling is tied to the prior ventricular contraction and late active filling is independently timed by the sinus rate, the pAVI controls the timing relationship between A-wave and ventricular contraction.

As will be described in detail below, the succeeding system and method for managing atrioventricular interval during cardiac resynchronization therapy overcomes the drawbacks of existing methods. For example, existing strategies that calculate the optimal pAVI as a fixed percentage of the PR interval (right iAVI) are biased against advancing left ventricular activation sufficiently to achieve maximum evidence of ventricular activation fusion. The reason for this is that the PR interval (right iAVI) does not account for left ventricular activation time. Therefore, biventricular pAVIs that reach a pre-defined stopping point as a fixed percentage of the PR interval will fail to advance left ventricular activation by a value at least equal to RVAT, which is the minimum magnitude of incomplete left ventricular pre-excitation.

Similarly, existing strategies that calculate the optimal pAVI based on the timing of the local left ventricular EGM are biased towards atrial truncation. The reason for this is that the left ventricular EGM is often recorded very late within the LVAT. Therefore, biventricular pAVIs that reach a pre-defined stopping point based on advancement of the left ventricular EGM may excessively advance left ventricular activation to a value within a range defined by right ventricular activation offset and left ventricular EGM. The potential consequence of this is that left ventricular activation collides with, or precedes left atrial activation offset.

A related source of variability is that the timing of the left ventricular EGM is dependent on the left ventricular stimulation site. Left ventricular EGM sites earlier within the LVAT may reduce the risk of atrial truncation, whereas later left ventricular EGM sites may increase the risk for reasons outlined above.

These considerations frame a significant clinical concern and challenge to CRM device programming regarding AVI management. Because generation of maximum evidence of ventricular activation wavefront fusion requires that biventricular paced activation replace native ventricular activation, pAVIs substantially shorter than the iAVI, commonly accompanied by sequential interventricular timing such as left ventricular stimulation first, are applied. The consequence of this arrangement is that it is much less likely that pAVIs during cardiac resynchronization therapy will be "too long." Rather, it is far more likely that pAVIs sufficiently short to generate maximum evidence of ventricular activation fusion will inadvertently induce truncation or block of late-active filling, such as when pAVI is "too short." This effect is a particular concern when the baseline PR interval, iAVI, is short.

Methods for recognition and correction of atrial sensing latency in order to enable leniency in primary pacing control parameters, such as increases in pAVI and shortening of left ventricular pre-excitation timing during interventricular pacing, that reduce the risk of left ventricular filling abnormalities such as diastolic dysfunction without compromising maximum evidence of ventricular activation wavefront fusion are described below.

The limitation of existing CIED-based strategies for optimizing AV resynchronization is that while the timing of left ventricular stimulation is known, the timing of left atrial electromechanical activation is not. Consequently, no existing CIED-based system can provide evidence that the primary pacing control parameters necessary to achieve maximal evidence of ventricular activation wavefront fusion do not result in left ventricular filling abnormalities, with particular attention on truncation of diastolic late active left ventricular filling, that is, A-wave truncation and atrial transport block. While it is conceivable that a multiplicity of novel pacing leads may eventually provide timing information regarding LA electromechanical activation, none currently exist.

It has been recognized that under certain conditions maximum evidence of ventricular activation wavefront fusion is not generated despite proper automatic or selectable adjustments to the usual critical pacing control parameters, including, but not limited to, recalibration of pAVI timing, interventricular ("V-V") timing, and pacing stimulus output voltages.

Figure 6:
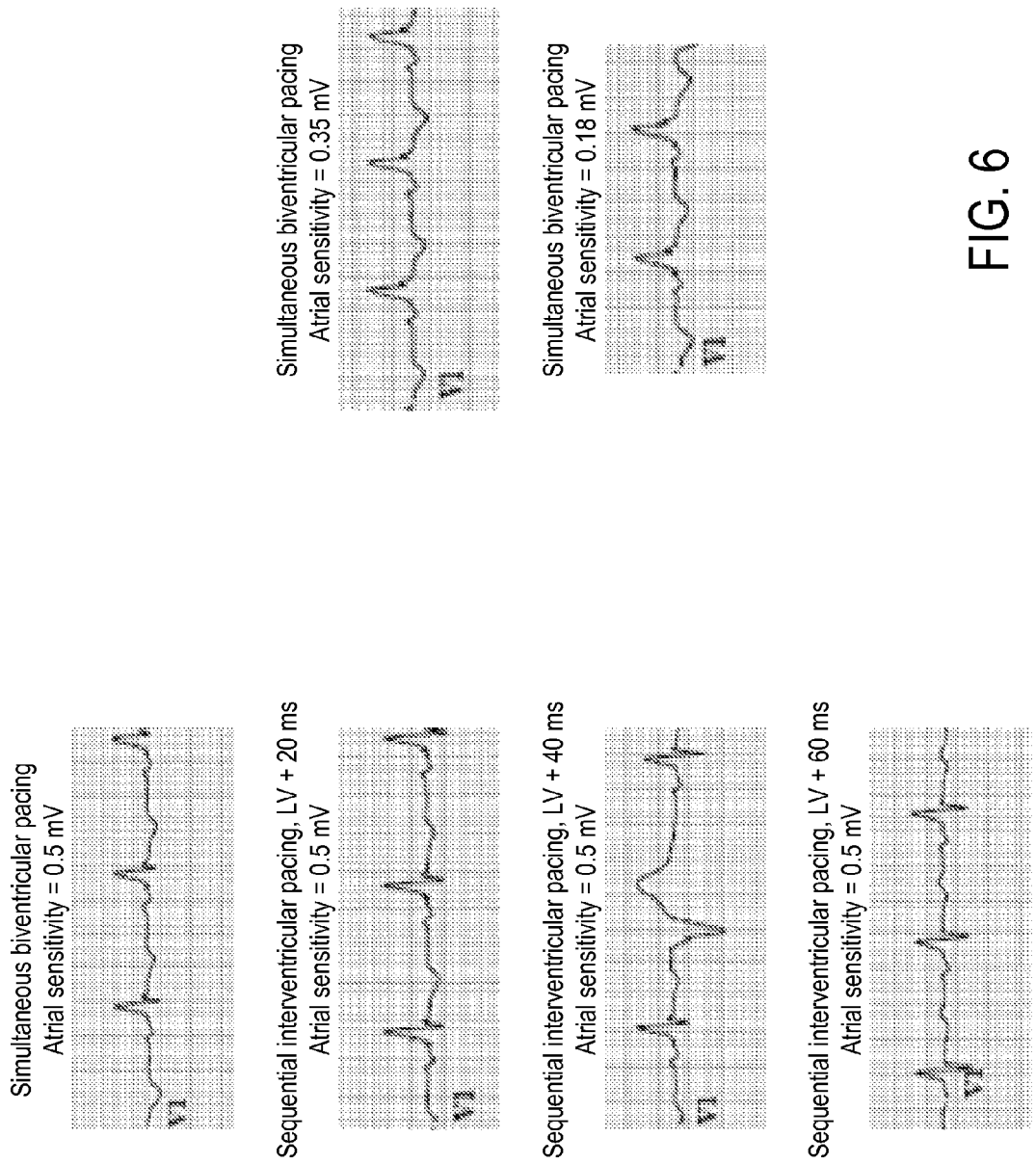
FIG. 6 is a pictorial illustration of the effect of changing atrial sensitivity to overcome incomplete ventricular activation wavefront fusion due to atrial sensing latency.

This condition is recognized by the following features. Left ventricular stimulation is performed form a site capable of reversing ventricular activation, which is confirmed by surface ECG QRS hieroglyph analysis; however, expected patterns of global ventricular activation fusion are reduced or absent despite manipulation of the usual critical pacing control parameters. In this example, a QRS hieroglyphic pattern of incomplete ventricular activation fusion persists despite short pAVI, around 100 milliseconds ("ms"), and progressive advancement of left ventricular stimulation with sequential biventricular pacing, as illustrated in FIG. 6. As shown by the four ECG signals from pivotal lead V1 illustrated on the left-hand side of FIG. 6, progressively earlier activation of the left ventricle yields no change in the global ventricular activation pattern (persistent Rs glyph), but increases the risk of diastolic dysfunction, that is, pAVI is potentially "too short." On the other hand, as shown by the two ECG signals from pivotal lead V1 illustrated on the right-hand side of FIG. 6, an increase in atrial sensitivity, yields increased evidence of ventricular activation fusion evidence (monophasic R glyph) despite simultaneous BV activation (e.g., even in the absence of V-V pacing, thereby reducing the risk that the pAVI is "too short").

A correctable cause of this paradoxical failure to advance left ventricular activation and generate maximum evidence of ventricular activation fusion is functional atrial undersensing, in which delayed recognition of the onset of local atrial electrical activation during atrial sensing operation, or sensing latency, occurs. The result of this behavior is that the pAVI starts later than the intrinsic AVI ("iAVI"). During LBBB, the right ventricle remains activated by intrinsic conduction, whereas activation to the left ventricle is delayed due to slow myocardial conduction. During biventricular pacing, right and left ventricular activation are controlled by the timing of the pacing stimuli, which follow atrial sensing at the programmed AVI. The programmed AVI is always less than the native PR interval so that both the right and left ventricle are activated earlier than would have occurred during native conduction. In this manner, biventricular pacing controls right and left ventricular activation, corrects left ventricular conduction delay due to LBBB, and generates ventricular activation wavefront fusion.

Because the biventricular pacing stimuli are emitted at the end of the pAVI, there is a mismatch between physiologic AVI, the time from atrial electrical activation to the biventricular pacing stimuli, and the pAVI in the presence of atrial sensing latency. Consequently, emission of the biventricular pacing stimulus is delayed relative to the true onset of atrial electrical activation. This has the effect of delaying left ventricular activation, which manifests as a failure to generate increasing evidence of activation fusion despite progressive shortening of the pAVI.

In the absence of atrial sensing latency, the pAVI starts with the onset of the atrial activation, identified by a P-wave. In the presence of atrial sensing latency, the start of the pAVI is delayed relative to onset of atrial activation with the result that the time that biventricular pacing advances native ventricular activation is reduced. The consequence of these timing relationships is that the left ventricular conduction delay due to LBBB is only partially corrected, manifest as incomplete ventricular activation fusion on the ECG. Increase in programmed atrial sensitivity eliminates atrial sensing latency so that the pAVI starts with the onset of atrial activation. As used herein, the term "atrial sensitivity" refers to the sensitivity on an intracardiac electrode in electrical communication with either the left or right atrium. The consequence of eliminating atrial sensing latency is that the time that biventricular pacing advances native ventricular conduction is further advanced. In turn, this results in complete correction of left ventricular conduction delay, manifest as maximal ventricular activation fusion, evidenced by expected changes in QRS glyphs or global measures of activation reversal.

By way of example, and referring again to FIG. 6, an increase in atrial sensitivity from 0.35 to 0.18 mV, while holding all other pacing control parameters constant, including pAVI, results in maximal evidence of ventricular activation fusion, indicated by greater amplitude of R-waves in pivotal lead V1. The increase in atrial sensitivity synchronizes local atrial electrogram sensing with the onset of the P-wave. The result of this synchronization is that the pAVI is equal to the effective AVI ("eAVI", see below) and the PR interval measurable on the biventricular paced surface ECG is shortened because the pAVI is initiated earlier. A shorter PR interval is due to earlier delivery of biventricular stimulation, relative to P-wave onset, with the consequence that left ventricular activation is further advanced and maximal evidence of ventricular activation fusion is generated.

At a lower atrial sensitivity, the pattern of maximum activation fusion is incomplete, whereas at a higher atrial sensitivity, such as around 0.18 mV, the pattern of activation fusion is maximized, confirming the role of atrial sensing latency in failure to completely advance left ventricular activation in order to generate maximum ventricular activation fusion.

Atrial sensing latency is frequently an unrecognized cause of failure to achieve maximum evidence of ventricular activation wavefront fusion. Failure to advance left ventricular activation due to atrial sensing latency is more likely to occur among patients with shorter PR intervals. This is a clinically important observation because pAVIs sufficiently short to generate maximum evidence of ventricular activation fusion are more likely to cause truncation of left ventricular filling when the baseline PR is short. This situation is potentially aggravated by simultaneous application of sequential interventricular pacing, such as left ventricular stimulation preceding right ventricular stimulation. Correction of atrial sensing latency in this situation allows advancement of left ventricular stimulation sufficient to achieve maximum evidence of ventricular activation fusion at longer pAVIs and without the need for sequential interventricular ("V-V") pacing, thereby reducing the risk of compromising diastolic function.

Adjustments to atrial sensitivity can be incorporated into the aforementioned systems and methods for titrating maximum evidence of ventricular activation wavefront fusion, such as the method described above in relation to FIG. 4. It is contemplated that atrial sensitivity adjustments would be invoked when failure to achieve maximum evidence of ventricular activation fusion is recorded after manipulation of the primary pacing control parameters, such as pAVI and interventricular timing, or when certain alert conditions exist, such as a short iAVI (e.g., PR interval less than 200 ms).

When a change in atrial sensitivity is made, a reassessment of (1) evidence of ventricular activation wavefront fusion and (2) emergence of far-field R-wave oversensing is performed. The lowest increase in atrial sensitivity that achieves maximal evidence of ventricular activation fusion is selected in order to minimize the risk of far-field R-wave oversensing. In some situations, the optimal atrial sensitivity for ventricular activation fusion results in far-field R-wave oversensing that cannot be eliminated. In such instances, rather than compromise ventricular activation fusion, pacing control parameter counter-measures are invoked to minimize the incidence and clinical consequences of far-field R-wave oversensing, such as adjustments to post-ventricular atrial blanking, atrial blanking, and mode switching control parameters.

Like other pacing control parameters, increases in atrial sensitivity may be automatically or semi-automatically triggered by certain clinical conditions or programming combinations of primary pacing control parameters necessary to achieve maximum evidence of ventricular activation fusion. For example, an alert could be triggered by a short PR interval (or CIED-measured timing surrogate, such as iAVI) because failure to advance left ventricular activation due to atrial sensing latency is more likely to occur in patients with short PR intervals or iAVI, such as those below 200 ms. Further, short PR intervals and iAVIs increase the odds that extreme adjustments of primary pacing control parameters, such as pAVI and interventricular (V-V) timing, are required to achieve maximum evidence of ventricular activation fusion. In this situation, very short pAVIs, accompanied by interventricular (V-V) timing (left ventricle first) increase the likelihood that diastolic function, such as left ventricle filling, will be compromised.

Accordingly, recognition and elimination of atrial sensing latency enables leniency in primary pacing control parameters, such as increases in pAVI and shortening of left ventricular pre-excitation timing during interventricular (V-V) pacing, that reduce the risk of LV filling abnormalities without compromising maximum evidence of ventricular activation wavefront fusion.

Because it is not currently possible to directly time left atrial electromechanical activation, an alternate approach is to estimate the true intrinsic, or baseline, left atrium-left ventricle ("LA-LV") electrical coupling time. This estimate serves as the outer bound for the pAVI during advancement of left ventricular activation. The time difference between this outer bound and the minimum pAVI raising concern for truncation of diastolic late active LV filling, such as less than 50 ms or clinician selectable, establishes the safe range for manipulation of the pAVI and interventricular (V-V) timing to achieve maximum evidence of ventricular activation wavefront fusion while minimizing risk of restrictive pattern diastolic dysfunction. In this manner, the risk of A-wave truncation is minimized rather than instead of attempting to achieve "optimal" AV resynchronization across a broad range of pAVIs, which is impractical given limitations mentioned above. Thus, titration of maximum evidence of ventricular activation fusion is prioritized while minimizing risk of A-wave truncation due to pAVIs that are "too short."

Timing of atrial and ventricular electrical activation can be estimated by analysis of the model of global cardiac electrical activity derived from surface ECG measurements integrated with multiple CIED EGM timing markers. In performing such an estimation, the end of left atrial activation and the beginning of left ventricular activation are established. This interval describes the true native LA-LV coupling time, which is measured as the time between left atrial activation offset and left ventricular activation onset.

The model of cardiac electrical activity described above further contains information pertaining to the timing of atrial and ventricular activation. The duration of the P-wave represents total atrial activation time ("AAT"), and the earliest deflection of the P-wave in any lead indicates the onset of right atrial activation. It is assumed that the latest termination of the P-wave in any lead represents the end of left atrial electrical activation. Since the duration of atrial electrical activation varies by regional point-of-view on the surface ECG, the latest termination of any P-wave in any anatomic region is taken to indicate the end of left atrial activation. Therefore, the atrial activation time is measured as the duration of time between the earliest P-wave onset and the latest P-wave termination across all surface ECG leads.

Interventricular conduction delay, such as bundle branch block, results in sequential ventricular electrical activation. This is typically registered on the surface ECG as a "split" or "notched" QRS complex. The first notch indicates the transition point between sequential monoventricular electrical activation. The portion of the QRS complex that occurs before the notch is composed by the first chamber activated, whereas the portion of the QRS complex that occurs after the notch is composed by the second, delayed chamber activated.

The earliest first upstroke of the left bundle branch block QRS complex in any ECG lead indicates the onset of right ventricular activation conduction. The earliest first notch in the QRS complex in any ECG lead indicates the transition point between the end of right ventricular activation and the onset of left ventricular activation due to left bundle branch block. The latest return of the QRS complex to baseline in any ECG lead indicates the termination of delayed left ventricular activation due to left bundle branch block.

The model of cardiac electrical activity described above further includes information pertaining to intrinsic atrioventricular intervals ("iAVIs") and LA-LV coupling time.

The time from the earliest deflection of the P-wave in any lead (right atrial activation onset) to the earliest first upstroke of the QRS complex (onset of right ventricular activation due to right bundle branch conduction) in any lead indicates the minimum right iAVI. The time from the earliest deflection of the P-wave in any lead to the earliest notch in the QRS complex in any ECG lead indicates the maximum right iAVI. The difference between the minimum and maximum right iAVI is the RVAT. The time from the latest termination of the P-wave in any lead (left atrial activation offset) to the earliest notch in the QRS complex in any lead (left ventricular activation onset) indicates the minimum left iAVI. The time from the latest termination of the P wave in any lead (left atrial activation offset) to the latest return of the QRS complex to baseline in any lead (left ventricular activation offset) indicates the maximum left iAVI. The difference between the minimum and maximum left iAVI is the LVAT.

Therefore, the time from the end of the latest terminating P-wave to the inflection point (nadir) of the first notch in the QRS complex which yields the longest $LVAT_{max}$ is the LA-LV electrical coupling time. This establishes the outer bound for manipulation of the pAVI and interventricular timing to titrate maximum evidence of ventricular activation wavefront fusion.

In typical left BBB conduction delay targeted for multisite pacing therapy, the right ventricle is activated first and the left ventricle is activated second. Because multiple notches in the QRS components during left BBB may occur due to myocardial scar, the first notch is assumed to indicate the transition between right ventricular and left ventricular depolarization. Some exceptions are necessary due to potentially confounding effects of myocardial scar on QRS notching. Notching in the first 40 ms of the S-wave in leads V1 or V2 is excluded since this indicates scar in the QRS score.

Right ventricular activation time ("RVAT") is measured as the time between QRS onset and the first notch in any of two or more adjacent ECG leads by anatomic region. These regions are anatomically designated as apical (leads I, V5, V6), anterior-superior (leads I, aVL), anterior-septal and posterolateral (leads V1-V2), anterior (leads V3-V4), and inferior (leads II, III, aVF).

Left ventricular activation time ("LVAT") is calculated as, $$LVAT = QRS_d - RVAT \quad (1);$$

where $QRS_d$ is the duration of the QRS complex in milliseconds. The longest or maximum LVAT, $LVAT_{max}$, is an independent predictor of the probability of reverse volumetric left volumetric remodeling during multisite pacing therapy, as will be described below in detail. Thus, increasing $LVAT_{max}$ anticipates a higher probability of reverse volumetric remodeling, assuming that ventricular conduction delay is sufficiently corrected and scar volume is not prohibitive. LVAT varies by anatomic region and the longest LVAT ($LVA_{max}$) are most often recorded in the inferior surface leads. Therefore, determination of ventricular activation time must be performed for all anatomic regions in order to determine the true $LVAT_{max}$. Occasionally, QRS notching is absent despite significant ventricular conduction delay. In the event that QRS notching is absent, a regression formula for estimating $LVAT_{max}$, derived from the numerical relationship between QRS duration and $LVAT_{max}$ can be applied. This numerical relationship specifies that $$LVAT_{max} = -35.839 + 0.763 \cdot QRS_d + 0.000619 \cdot QRS_d^2 \quad (2).$$

A variety of EGM QRS glyph templates, representing a CIED-based reduced lead set, are collected. These provide an accurate and reliably reproducible composite surrogate for surface ECG QRS hieroglyphs and represent various views of global ventricular activation. The use of EGM QRS glyph templates from multiple recording sources increases the accuracy of CIED-based VAT measurements. It is contemplated that a combination of near- and far-field EGM QRS glyph templates would be employed. The use of multiple EGM QRS glyph templates increases the reproducibility and accuracy of global ventricular activation imaging for future automatic adjustments.

Figure 7:
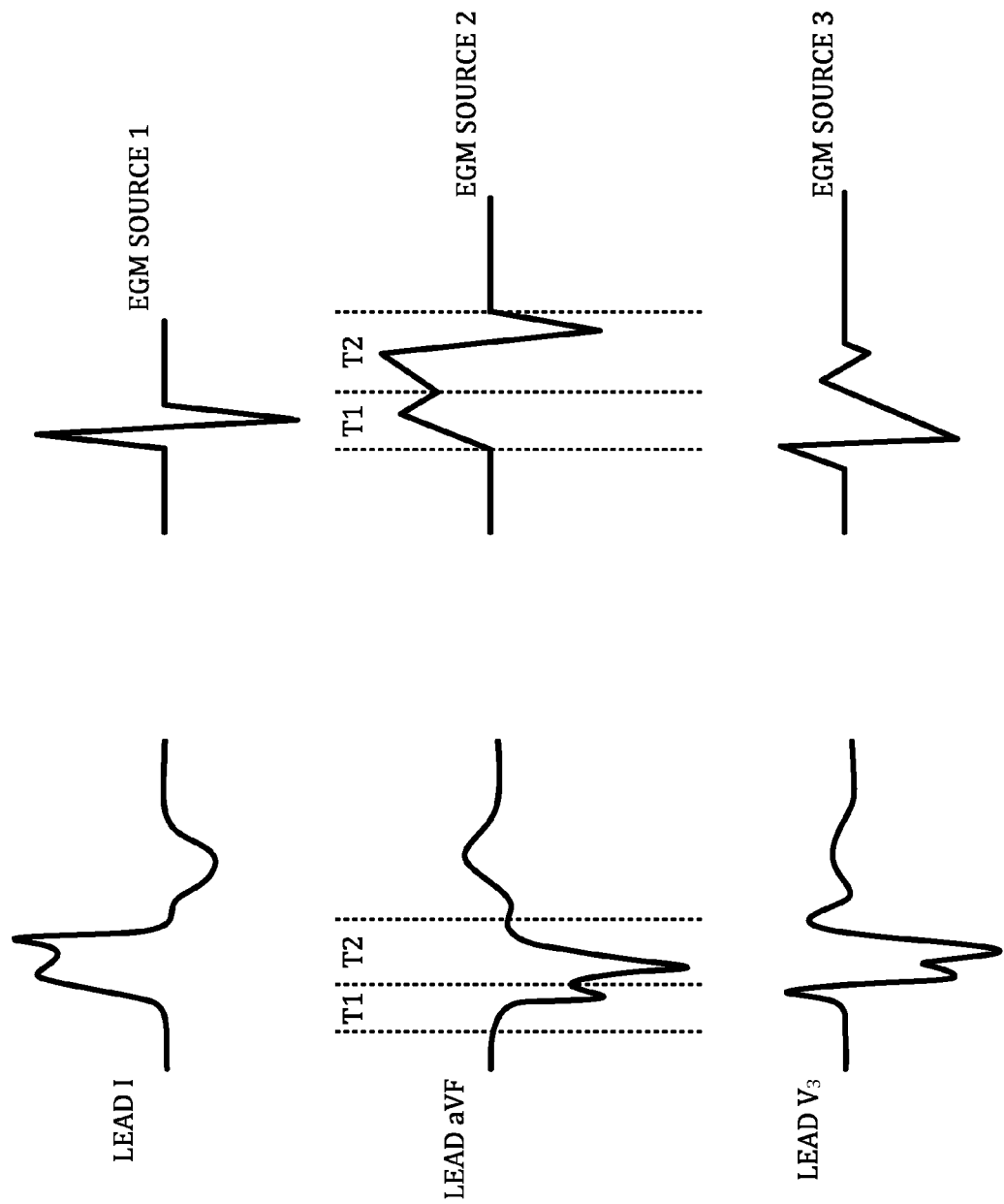
FIG. 7 is a pictorial illustration of a set of exemplary surface electrocardiograph ("ECG") lead signals and CIED-based electrogram ("EGM") signals showing the calculating of a ventricular activation time on both the ECG and EGM signals.

Referring now to FIG. 7, since $LVAT_{max}$ varies by anatomic region, multiple CIED EGM glyph templates will be screened and correlated with the surface ECG measurements contained in the model of cardiac electrical activity. The EGM QRS glyphs are examined for notching, indicative of sequential ventricular electrical activation. The QRS duration, RVAT, and LVAT are measured from the acquired EGMs in a similar manner as described for the surface ECG signals above. For example, time from onset (first deflection from baseline in any direction) to first notch or peak in the real-time, pacing-inhibited (or right univentricular paced) biventricular EGM is assumed to indicate RVAT. This time is shown as T1 in FIG. 7. Further, LVAT is calculated as, $$LVAT = QRS_{d,EGM} - RVAT \quad (3);$$

where $QRS_{d,EGM}$ is the EGM QRS glyph duration in milliseconds. This time is shown as T2 in FIG. 7.

The $LVAT_{max}$ value derived from the EGMs is designated as the EGM LVAT that most closely approximates the $LVAT_{max}$ recorded on the surface ECG and contained in the model of cardiac electrical activity. This is not necessarily the longest EGM $LVAT_{max}$ because differences in EGM QRS glyph and ECG QRS glyph durations exist. In the situation where one or more EGM $LVAT_{max}$ values exceed the $LVAT_{max}$ value in the model of cardiac activity, the EGM $LVAT_{max}$ value that most closely approximates the $LVAT_{max}$ in the model is selected.

If EGM glyph QRS notching is absent during native ventricular activation or paced right univentricular activation, $LVAT_{max}$ is derived using the regression formula for QRS duration described above in Eqn. (2). For example, the QRS glyph from source 1 lacks QRS notching and is therefore either rejected for VAT calculation, or the regression formula in Eqn. (2) is employed. In this situation, the longest EGM glyph QRS duration recorded from any source, or averaged across sources, is used to calculate $LVAT_{max}$. Alternately a composite of EGM glyphs may be used to provide a more accurate global measure of $LVAT_{max}$. In this situation, RVAT, LVAT, and QRS duration are recorded across multiple source EGM glyphs to provide a more complete assessment of global ventricular activation. These values are averaged in order to provide a more balanced measure of VAT.

It is contemplated that the determination of EGM glyph QRS $LVAT_{max}$ is done at the time of CIED multisite pacing therapy initiation. It is unlikely that redetermination of ECG-based VATs will be routinely necessary. Periodic checks of pacing-inhibited real-time EGM QRS glyph $LVAT_{max}$ templates are, however, likely to be made. The purpose of periodic surveillance is to detect a clinically relevant change in baseline ventricular conduction characteristics. Such checks can be automatically scheduled at selectable or default time intervals, or automatically triggered by a change in patient or pacing condition, such as emergence of pacemaker dependence. Certain situations could trigger an alert condition where redetermination of ECG and EGM based VATs is advised. For example, a significant change of more than ten percent in periodically determined EGM glyph QRS $LVAT_{max}$ values could be indicative of a clinically relevant change in baseline ventricular activation time and sequence. Such an observation could automatically trigger a reminder to repeat semi-automatic ECG and EGM-based measurements at next follow-up.

The EGM glyph QRS $LVAT_{max}$ is subsequently used to provide diagnostic information, such as prediction models for probability of reverse volumetric remodeling and timing instructions during multisite pacing, as specified below.

Atrial and biventricular electrical activation times during sinus rhythm (atrial pacing-inhibited) derived from the surface ECG may be characterized by CIED-based EGM surrogates. The time from the earliest deflection of the P-wave in any lead to the time of local right atrial EGM during sinus rhythm (atrial pacing-inhibited) is the right atrial sensing latency time. The time from earliest upstroke of the QRS complex in any lead to the time of the local right ventricular EGM is the right ventricular sensing latency time. The time from the local right atrial EGM to the local right ventricular EGM is the right pAVI, which is the CIED surrogate of the minimum right intrinsic iAVI. Therefore, the CIED effective right pAVI ("eAVI") is determined as, $$eAVI_{right}=(pAVI_{right}+SL_{RA})-SL_{RV} \quad (4);$$

where $SL_{RA}$ is the right atrial sensing latency and $SL_{RV}$ is the right ventricular sensing latency. The CIED surrogate of the total interventricular activation time is the time from local right ventricular EGM to the local left ventricular EGM. This inaccurately estimates true interventricular activation time because of right ventricular sensing latency, left ventricular sensing latency, and variable timing of left ventricular EGM relative to QRS offset as determined by the left ventricle lead position.

In a similar manner, LA-LV electrical coupling times and CIED-EGM surrogates during sinus rhythm (atrial-pacing inhibited) can be calculated. The pAVI is measured from the time of atrial sensing to the scheduled biventricular paced event. The CIED effective pAVI is measured from right atrial onset to the scheduled biventricular paced event. Therefore, the effective pAVI exceeds the pAVI when sensing latency is present. The CIED effective left sinus rhythm is therefore calculated as, $$eAVI_{left,sinus}=(pAVI_{right}+(RV_{EGM}{\rightarrow}LV_{on}))-(RA_{EGM}{\rightarrow}LA_{off}) \quad (5);$$

where $(RV_{EGM}{\rightarrow}LV_{on})$ is the time from right ventricular EGM to left ventricular onset and $(RA_{EGM}{\rightarrow}LA_{off})$ is the time from right atrial EGM to left atrial offset.

During atrial pacing, adjustments are made for atrial capture latency. Atrial capture latency is the time from emission of the atrial pacing stimulus to the earliest deflection of the P-wave in any lead. Note that atrial activation time increases during atrial pacing due to intra- and interatrial conduction delay. The atrial paced pAVI is measured from the time the atrial pacing stimulus is emitted to the scheduled biventricular paced event. The effective pAVI is measured from right atrial activation onset to the scheduled biventricular paced event. Therefore, the atrial-paced pAVI exceeds the effective pAVI when capture latency is present. The CIED effective left atrial paced pAVI is, $$eAVI_{left,pace}(pAVI_{right,pace}+(RV_{EGM}{\rightarrow}LV_{on}))-(AP{\rightarrow}LA_{off}) \quad (6);$$

where $pAVI_{right,pace}$ is the right atrial paced pAVI, $(RV_{EGM}{\rightarrow}LV_{on})$ is the time from right ventricular EGM to left ventricular onset, and $(AP{\rightarrow}LA_{off})$ is the time from atrial pacing stimulus to left atrial offset.

The linkage of surface ECG analysis of atrial and biventricular activation times to CIED EGM timing measurements are integrated to provide an estimate of the permissible range of pAVIs to titrate maximum ventricular activation wavefront fusion while minimizing risk of reduce late diastolic LV filling.

Figure 8:
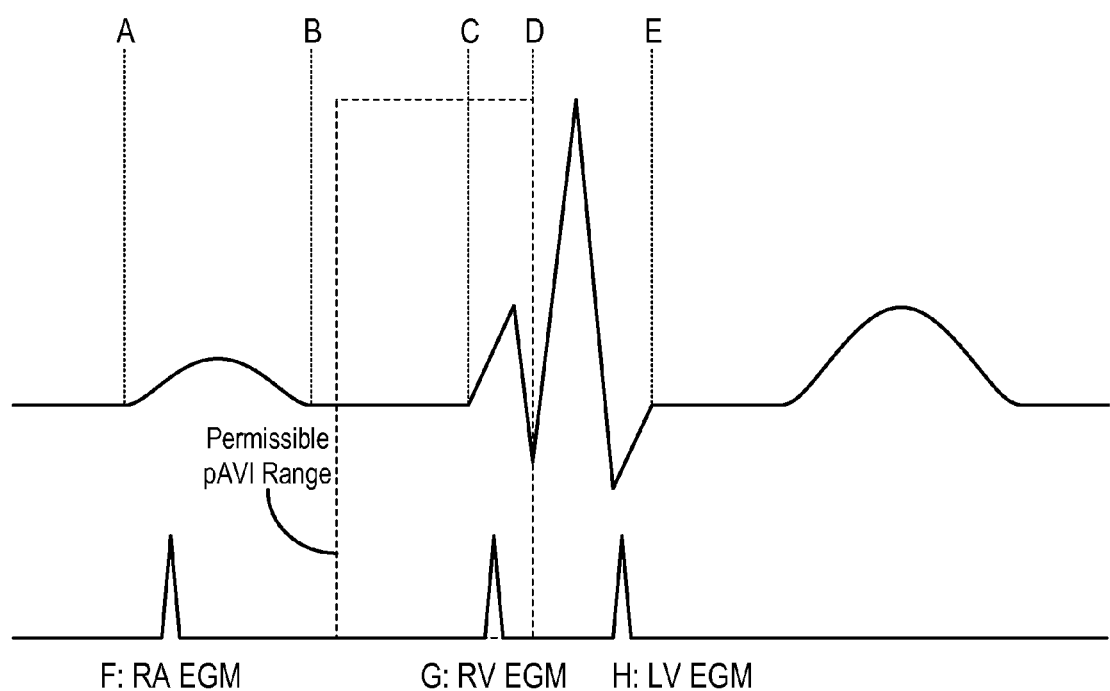
FIG. 8 is a pictorial illustration of an exemplary surface ECG signal and corresponding EGM signals.
Figure 9:
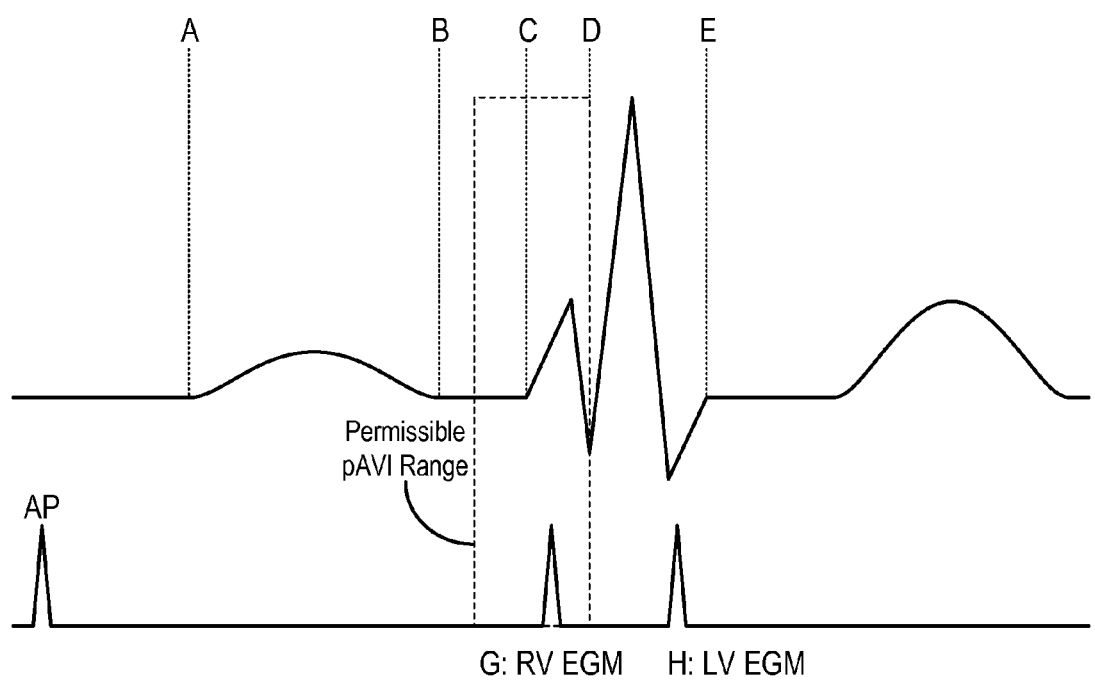
FIG. 9 is a pictorial illustration of an exemplary surface ECG signal and corresponding EGM signals during atrial pacing with no increased atrioventricular conduction time.
Figure 10:
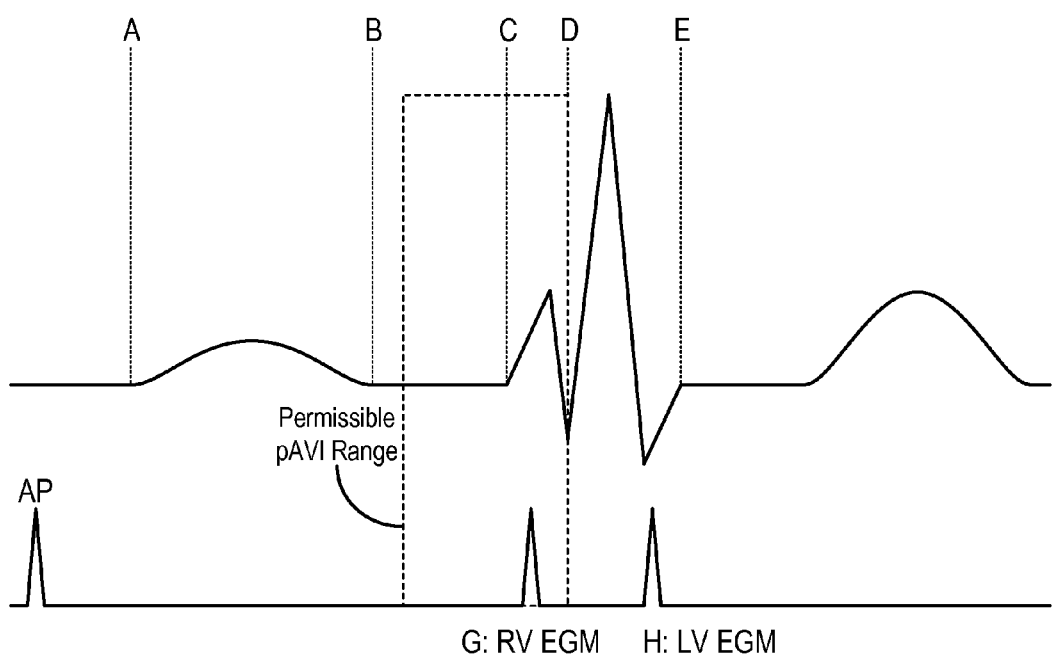
FIG. 10 illustration of an exemplary surface ECG signal and corresponding EGM signals during atrial pacing with increased atrioventricular conduction time.

Referring now to FIGS. 8-10, an exemplary ECG signal, corresponding EGM signals, and relevant timing parameters and metrics are illustrated, as described in Table 2. The notations listed in Table 2 are defined as follows. By way of example, A-C identifies the duration of time between time point A and time point C on FIGS. 8-10. Here, the duration A-C identifies the right intrinsic atrioventricular interval ("iAVI"), or atrioventricular conduction time ("AVCT"). In each of FIGS. 8-10, the dashed box indicated the range of permissible pAVI values for maintaining the desired ventricular activation fusion without induced undesirable diastolic dysfunctions.

TABLE 2

| Notation | Timing Parameter or Metric |
| --- | --- |
| A | Onset of right atrial activation |
| B | Offset of left atrial activation |
| C | Onset of right ventricular activation (RBB conduction) |
| D | Offset of RV activation (RBB conduction)/onset of LV activation (LBB conduction) |
| E | Offset of LV activation (LBB conduction) |
| A-B | Atrial activation time (AAT) |
| A-C | Right $iAVI_{min}$, atrioventricular conduction time (AVCT) |
| A-D | Right $iAVI_{max}$ |
| B-D | Left $iAVI_{min}$, intrinsic LA-LV coupling time |
| B-E | Left $iAVI_{max}$ |
| C-D | RVAT |
| D-E | LVAT ($QRS_d$-$RVAT_{max}$) |
| C-E | True interventricular conduction time, $QRS_d$ |
| A-F | RA sensing latency |
| F-G | Right pAVI |

TABLE 2-continued

| Notation | Timing Parameter or Metric |
|---|---|
| ((F-G) + (A-F)) − (C-G) | CIED effective right pAVI |
| G-H | CIED-based interventricular conduction time |
| F-B | Time from RA EGM to LA offset |
| G-D | Time from RV EGM to LV onset |
| ((F-G) + (G-D)) − (F-B) | CIED effective left pAVI (left sinus rhythm) |
| AP-A | Atrial capture latency |
| ((AP-G) + (G-D)) − (AP-B) | CIED effective atrial paced left pAVI |

Referring particularly to FIG. 8, an exemplary effective left sinus rhythm pAVI of 300 ms, which is the CIED EGM derived surrogate for LA-LV electrical coupling time on the surface ECG, is illustrated. This defines the minimally effective biventricular pAVI since left ventricular stimulation will occur simultaneously with native left ventricular activation onset and, therefore, left ventricular activation will not be advanced. Assuming the minimum permissible LA-LV electrical coupling time is 50 ms (to prevent atrial truncation) and the P-wave duration (atrial activation time) is 80 ms, the minimum permissible biventricular pAVI is 130 ms. Therefore, the effective left sinus rhythm biventricular pAVI operating range is 130-300 ms, thereby defining the permissible pAVI range 802. As the biventricular pAVI is reduced from 300 ms to 130 ms, left ventricular activation is advanced, thereby titrating ventricular activation wavefront fusion. Maximum evidence of ventricular activation wavefront fusion is generated using the methods described above. The biventricular left pAVI outer bound (e.g., 300 ms) is defined as the minimally effective pAVI, whereas the inner bound (e.g., 130 ms) is defined as the maximally effective pAVI within the operating constraints defined by the intrinsic LA-LV electrical coupling time and the minimally acceptable LA-LV coupling time during bi ventricular pacing.

The effect of applying the maximally effective biventricular pAVI (e.g., 130 ms) which does not violate the minimally acceptable LA-LV coupling time (e.g., 50 ms) on right and left ventricular activation timing results in left ventricular activation that is advanced more than right ventricular activation due to baseline left ventricular conduction delay. In this example, left ventricular activation onset is advanced by 200 ms, activation at the left ventricular EGM is advanced by 300 ms, and left ventricular activation offset is advanced by 350 ms.

This example is extended to include some of the anticipated effects of atrial pacing on atrial-ventricular timing interval measurements in FIG. 9. Atrial pacing introduces atrial capture latency (time between emission of the atrial pacing stimulus and right atrial electrical activation) and an increase in atrial activation time (P-wave duration) due to intra- and interatrial conduction delay. The effect of an increase in atrial activation time, even in the absence of an increase in AV conduction time, is to delay the offset of left atrial activation, which reduces the pAVI permissible range. Assuming the minimum permissible LA-LV electrical coupling time is 50 ms (to prevent atrial truncation), an atrial pacing stimulus to atrial activation delay time of 50 ms, and an atrial activation time (P-wave duration) of 130 ms, the minimum permissible biventricular pAVI is 230 ms. Therefore, the effective left sinus rhythm biventricular pAVI operating range is 230-300 ms. In this example, the permissible pAVI range has been reduced by 100 ms.

As the biventricular pAVI is reduced from 300 to 230 ms, left ventricular activation is advanced, titrating ventricular activation wavefront fusion. Maximum evidence of ventricular activation wavefront fusion is generated using methods described above. The biventricular pAVI outer bound (e.g., 300 ms) is defined as the minimally effective pAVI, whereas the inner bound (e.g., 230 ms) is defined as the maximally effective pAVI within the operating constraints defined by the intrinsic LA-LV electrical coupling time and the minimally acceptable LA-LV coupling time during biventricular pacing.

The effect of applying the maximally effective left biventricular pAVI (e.g., 130 ms) which does not violate the minimally acceptable LA-LV coupling time (e.g., 50 ms) on right and left ventricular activation timing results in ventricular activation that is advanced more than right ventricular activation due to baseline left ventricular conduction delay. In this example, right ventricular activation is advanced by 20 ms, left ventricular activation onset is advanced by 100 ms, activation at the left ventricular EGM is advanced by 200 ms, and left ventricular activation offset is advanced by 250 ms.

This example is further extended to include the salutary effect of an increase in AV conduction time ("AVCT") during atrial pacing, or increase in heart rate by other means, on atrial-ventricular timing interval measurements in FIG. 10. Atrial pacing introduces atrial capture latency, an increase in atrial activation time due to intra- and interatrial conduction delay, and an increase in AVCT due to decremental AV conduction. The effect of an increase in atrial activation time is to delay the offset of left atrial activation, which narrows the pAVI permissible range, whereas the effect of an increase in AVCT is to delay the onset of left ventricular activation, which widens the pAVI permissible range.

Assuming the minimum permissible LA-LV electrical coupling time is 50 ms (to prevent atrial truncation), an atrial pacing stimulus to atrial activation delay time of 50 ms, and an atrial activation time (P-wave duration) of 130 ms, the minimum permissible biventricular pAVI is 230 ms. Therefore, the effective sinus rhythm BV pAVI operating range is 230-410 ms. The permissible pAVI range has been increased by 80 ms due to the counterbalancing effects of increased AVCT on the duration of diastolic filling time. As the biventricular pAVI is reduced from 410 to 230 ms, left ventricular activation is advanced, titrating ventricular activation wavefront fusion. Maximum evidence of ventricular activation wavefront fusion is generated using methods described above. The biventricular pAVI outer bound (e.g., 410 ms) is defined as the minimally effective pAVI, whereas the inner bound (e.g., 230 ms) is defined as the maximally effective pAVI within the operating constraints defined by the intrinsic LA-LV electrical coupling time and the minimally acceptable LA-LV coupling time during biventricular pacing.

The effect of applying the maximally effective biventricular pAVI (e.g., 130 ms) which does not violate the minimally acceptable LA-LV coupling time (e.g., 50 ms) on right and left ventricular activation timing results in left ventricular activation that is advanced more than right ventricular activation due to baseline left ventricular conduction delay. In this example, right ventricular activation is advanced by 100 ms, left ventricular activation onset is advanced by 180 ms, activation at the left ventricular EGM is advanced by 280 ms, and left ventricular activation offset is advanced by 330 ms.

The aforementioned method for AVI management can be incorporated into the previously described systems and methods for titrating maximum evidence of ventricular activation wavefront fusion including atrial sensitivity adjustments when failure to achieve maximum evidence of ventricular activation fusion is recorded.

The majority of integrated timing measurements made at baseline are fixed, such as RVAT, LVAT, interventricular conduction time, and sinus rhythm atrial activation time. Atrial and ventricular sensing and capture latencies and inter/intraatrial, paced atrial activation time, and ventricular conduction times remain generally constant across heart rates assuming stable sites of activation. Increases in iAVI during sinus rhythm or atrial pacing typically occur at increasing rates in the waking state and decreasing rates in the sleep state, and could be periodically reassessed by any of several methods known to those skilled in the art, including progressive extension of the pAVI, withholding of single schedule biventricular paced stimuli, temporary switching to a non-tracking mode, and so on.

Periodic recalculation of timing measurements could be triggered by a spontaneously recorded change in iAVI, such as shortening, lengthening, or absence due to emergence of AVB. Recalculation of timing measurements may also be automatically triggered during a programmer interface session when certain control parameters are changed, such as changes in atrial or ventricular pacing rate, atrial sensitivity, pAVI under different atrial rhythm conditions, change in interventricular interval, and so on, or when selected by the clinician in anticipation of change in critical pacing control parameters or in response to known change in clinical conditions.

The system and method described herein for AVI management is fully integrated with the above described systems and methods for automatically generating ventricular activation wavefront fusion, titrating maximum evidence of ventricular activation wavefront fusion, and determining ventricular activation times. In particular, the methods for AVI management and automatically increasing atrial sensitivity work synergistically to overcome failure to achieve maximum evidence of ventricular activation fusion and reduce risk of left ventricular diastolic filling abnormalities without compromising maximal evidence of ventricular activation wavefront fusion. It is contemplated that this approach will be particularly useful among patients with shorter PR intervals (iAVI) because pAVIs sufficiently short to generate maximum evidence of ventricular activation fusion are more likely to cause truncation of left ventricle filling (atrial transport block) when the baseline PR is short. Similarly, it is contemplated that this combined approach will reduce the risk of left ventricle filling abnormalities under conditions of increased atrial activation time.

Figure 11:
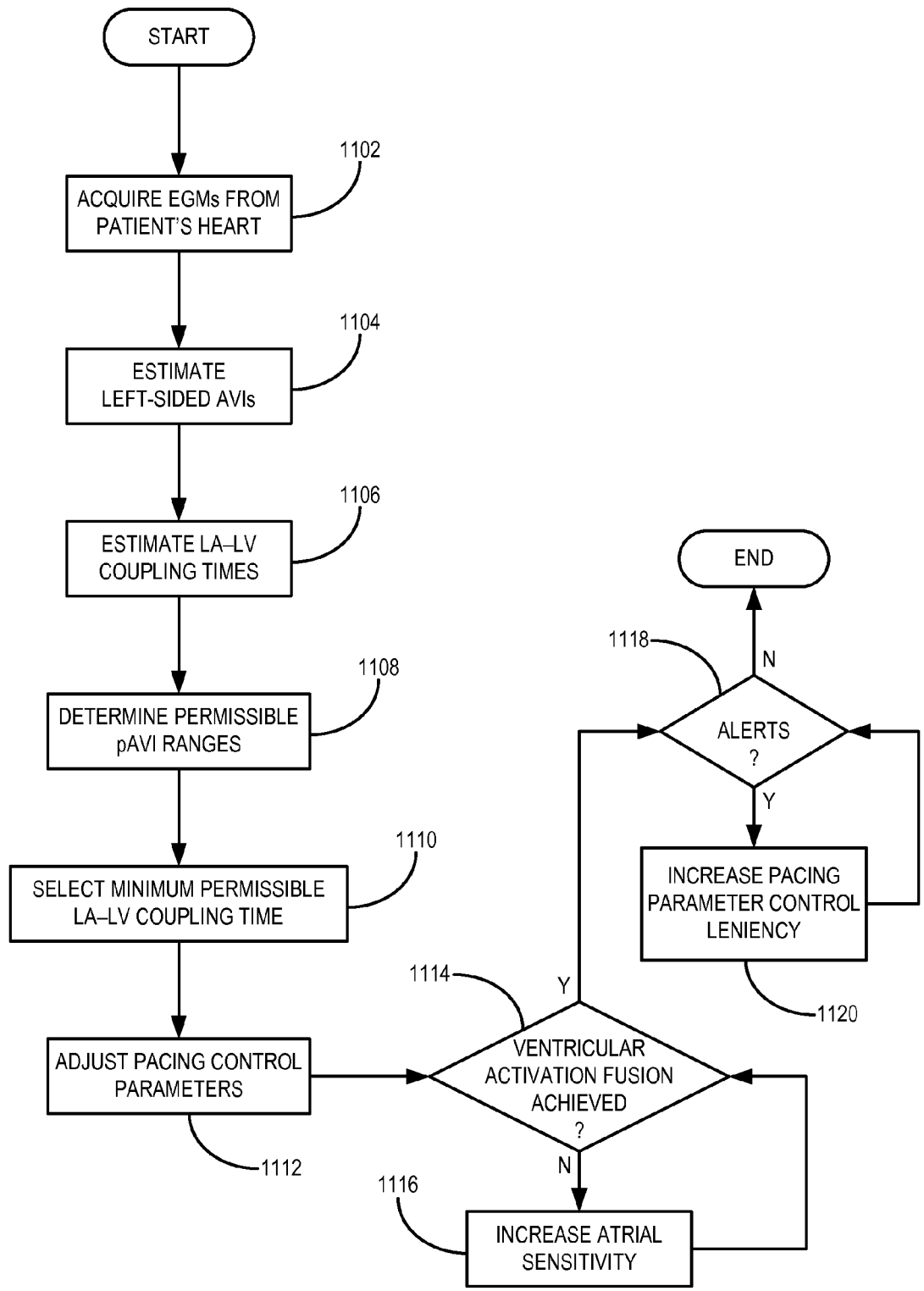
FIG. 11 is a flowchart setting forth the steps of an exemplary method for performing atrioventricular interval managed cardiac resynchronization therapy.

Referring now to FIG. 11, a flow chart setting forth the steps of an exemplary method for performing atrioventricular interval managed cardiac resynchronization therapy is illustrated. The method begins with the passive acquisition of electrograms ("EGMs") from a patient's heart by a cardiac rhythm management ("CRM") device implanted in the patient, as illustrated at step 1102. Next, left-sided AVIs, such as intrinsic AVI, pacemaker AVI, and effective AVI, are estimated as described above in detail, and as indicated at step 1104. Left-sided LA-LV electrical coupling times are also estimated as described above, and as indicated at step 1106.

Using the estimated AVIs and LA-LV coupling times, a range of permissible pAVI values is determined, as indicated at step 1108. The range of permissible pAVI values is determined by calculating the minimum and maximum permissible pAVI values that still maintain the desired ventricular activation fusion. A minimum permissible LA-LV coupling time is selected next, as indicated at step 1110.

Using the above determined timing metrics, the pacing control parameters of the CRM device are adjusted to ensure that the desired ventricular activation wavefront fusion is maintained, as indicated at step 1112. For example, pAVI may be adjusted within the permissible range of pAVI values to produce maximum evidence of ventricular activation fusion, as determined using the method described above in detail with respect to FIG. 4. A determination is made at decision block 1114 whether maximum evidence of ventricular activation fusion is observed. If not, atrial sensitivity is iteratively increased, as indicated at step 1116, until the maximum evidence of ventricular activation fusion is obtained.

A determination is then made whether an alert for diastolic dysfunction exists, as indicated at decision block 1118. Exemplary alert conditions include short PR interval, iAVI, pAVI, interventricular timing, or combinations thereof. If an alert condition exists, then the leniency in one or more pacing control parameters is increased, as indicated at step 1120. For example, the leniency in pAVI or interventricular timing may be increased while maintaining high atrial sensitivity and monitoring ventricular activation fusion.

The foregoing method is continuously operable by the implanted CRM device, such that pacing control parameters are automatically and routinely adjusted in real-time to maintain proper, synchronous ventricular activation.

ECG quantification of left ventricular scar volume is calculated using the QRS Score for left bundle branch block. The effects of scar on left bundle branch block surface registration translate as specific QRS hieroglyphic signatures. For example, they manifest as unopposed rightward electrical forces by infarct region, as shown below in Table 3.

TABLE 3

| Infarct Region | ECG Lead | QRS Glyph Signature |
| --- | --- | --- |
| Anterior-superior | I, aVL | qR, QR, rS |
| Apical | V5-V6 | qR, QR, rS |
| Inferior | II, aVF | qR, QR, rS |
| Anterior-septal | V1-V2 | QS to rS, RS, Rs |

Notching on the ascending limb of the S-wave in V1-V2 indicates posterolateral infarct. QRS score, each score point indicative of three percent left ventricular scar volume, has recently been shown to have an inverse relationship with the probability of reverse volumetric ventricular remodeling in adjusted models accounting for all other baseline and post-multisite pacing predictors of remodeling.

Since QRS score is a measure of ventricular scar volume, which is fixed, scar volume estimates need not be made on a periodically recurring basis. QRS score can be manually or automatically determined in less than five minutes using screen calipers and the surface ECG linked to the CIED user interface, as described above. This process may be automated by linking a series of queries by anatomic region to input variables for the QRS score using the programmed-based surface ECG. The QRS score may also be generated automatically by software dedicated to ECG analysis. Once composed, it is contemplated that the QRS score will remain static for the duration of follow-up unless overridden by the user.

It is desirable to provide an accurate and continuously updating estimate of the probability of reverse volumetric ventricular remodeling that can be reported to the clinician. Such estimates enable the clinician to understand the effects that changes to critical CIED operating parameters have on the probability of remodeling. Moreover, these estimates enable to clinician to identify the optimal control parameters for maximizing the odds of reverse ventricular remodeling.

Determination of a probability of reverse volumetric ventricular remodeling includes the following general stages. First, markers of ventricular scar volume are determined, ventricular activation times are calculated as described above, and global baseline ventricular activation sequences are determined as described above. Second, the QRS score for the determined ventricular scar volume is identified and provided to the CIED along with the calculated ventricular activation times. Then, ECG markers of ventricular activation times and global activation wavefront fusion are transferred from the model of cardiac electrical activity to CIED-based surface ECG surrogates in the form of multiple, complementary intracardiac, far-field (possibly including body surface) EGM QRS glyphs. Using the CIED-based EGM QRS glyphs, pacing control parameters are continuously adjusted to guarantee optimal global ventricular activation wavefront fusion on a continuous (e.g., beat-to-beat) or nearly continuous basis. Then, baseline predictors, such as QRS score for ventricular scar volume and ventricular activation times, and post-pacing predictors, such as ventricular activation fusion evidence, are compiled for the probability of reverse ventricular remodeling. These components are passed to a validated regression model for predicting probability of reverse volumetric remodeling and the probability of remodeling is output as a dedicated diagnosis in the CIED. Automatic updates of the probability model may be performed when substrate and post-pacing conditions change.

The values for the four component variables (QRS score, maximum left ventricular activation time $LVAT_{max}$, and two forms of post-pacing fusion evidence) are entered into a linear regression which yields an estimate of the odds of reverse remodeling. The regression equation is specified as follows. Probability of ten percent or more reduction in left ventricular end systolic volume ("LVESV") is given as, $$p = \frac{1}{1 - e^{-\alpha}}; \quad (7)$$

where, $$\alpha = \qquad (8)$$
$$-1.311 - 0.7428 \cdot \beta - 0.0985 \cdot \gamma + 0.0207 \cdot \delta + 0.5794 \cdot \varepsilon + 0.4301 \cdot \zeta;$$

$$\beta = \begin{cases} QRS & QRS \le 4 \\ 4 & QRS > 4; \end{cases} \quad (9)$$

$$\gamma = \begin{cases} 0 & QRS \le 4 \\ QRS - 4 & QRS > 4; \end{cases} \quad (10)$$

QRS is the QRS score points;

$$\delta = \begin{cases} LVAT_{max} & LVAT_{max} \le 125 \\ 125 & LVAT_{max} > 125; \end{cases} \quad (11)$$

$\varepsilon$ is 4.5 when the mean change in the R-wave amplitude measured in leads V1 and V2, as a proportion of baseline, is less then 4.5, and $\varepsilon$ is the mean change in the R-wave amplitude measured in leads V1 and V2, as a proportion of baseline when that value is greater than 4.5; and $\zeta$ is 1 when the patient has frontal plane axis shift and is zero otherwise.

The two baseline component variables (QRS score points and $LVAT_{max}$) in the prediction model are fixed at the level of myocardial substrate and, therefore, need to be measured only once, for example, at implantation or device initialization. The two post-pacing component variables in the prediction model are dynamic and responsive to changes in pacing conditions. Again, these post-pacing components are mean change in R-wave amplitude in leads V1 and V2 as a proportion of baseline, and left axis deviation ("LADEV") to right axis deviation ("RADEV") frontal plane axis shift. Accordingly, changes in pacing conditions translating as changes in measures of global ventricular activation will positively or negatively influence the odds of reverse remodeling. This provides an opportunity to re-calculate the odds of reverse remodeling in response to automatic or clinician-selected changes in pacing timing instructions and provide this updating information as a dedicated diagnostic. Currently, no such system exists in multisite pacing systems.

The regression formula in Eqns. (7)-(8) is used to automatically calculate the odds of reverse ventricular remodeling, which is defined as ten percent or more reduction in LVESV. For example, if QRS score points has a value of 12, $LVAT_{max}$ value of 87.0, mean change in R-wave amplitude in leads V1 and V2 as a proportion of baseline a value of 6.375, and LADEV to RADEV is set to 1, the predicted probability of remodeling is 70.2 percent. Automatic or clinician-selected adjustment in the timing of biventricular stimulation results in predictable and known changes in global ventricular activation, as described above in detail. Such changes are registered on surface ECG glyphs and translated to CIED EGM glyphs.

R-wave amplitudes are automatically or semi-automatically measured at baseline. Simultaneous biventricular pacing is initiated. Paced ventricular activation is analyzed with surface ECG leads. Digital templates of paced ventricular activation are presented side-by-side with the corresponding leads during baseline ventricular activation. A manual, semi-automatic, or fully automatic numerical comparison is made for evidence of maximum change in R-wave amplitude in the expected direction by each individual lead. Next, manual, semi-automatic, or fully automatic adjustments to ventricular pace timing control parameters are made and the QRS template acquisition and comparison process is repeated. Exemplary control parameter adjustments include manipulation of the pAVI (e.g., by shortening), or sequentially timed ventricular (V-V) pacing timing.

In the latter situation, the electrically delayed ventricle is stimulated at fixed or variable intervals prior to the early activated ventricle until maximal change in R-wave amplitude in the expected direction for each of the leads is recorded. This represents maximal evidence of paced activation wavefront fusion, which predicts probability of reverse ventricular remodeling.

Such changes in chamber timing parameters are expected to generate larger R-wave amplitudes in leads V1-V2 and increase frontal plane axis shift (LADEV to RADEV). Consider the example patient where mean change in R-wave amplitude in leads V1 and V2 is increased from six to twelve due to changes in pacing timing instructions. Holding the remaining three variables constant at the exemplary values reported above, then the predicted probability of reverse remodeling increases to 98.4 percent.

Alternately, or in addition to generating the numerical probability of reverse remodeling, the odds of reverse remodeling can be estimated using the format of global measure of changes in activation wavefront directionality. As described above in detail, a novel and specific method for quantifying the change in QRS glyph morphology by in the expected direction, by pivotal lead, is provided. This provides an alternate way of characterizing evidence for ventricular fusion using regional or global measures of change in maximum R-wave amplitude in the expected direction indicating activation wavefront reversal before and after pacing.

Since reverse remodeling predicts longer survival (reduced mortality) and improvement in signs and symptoms of heart failure, diagnostic reporting of the probability status of reverse remodeling may be important to the clinician. Such a tool provides visual evidence of the effect on odds of remodeling for automatic or manually selected changes in critical pacing control parameters that generate maximum evidence of activation wavefront fusion. One method of reporting the odds of reverse remodeling is simple numerical output. The four component variables of the remodeling regression equation are presented. The two baseline variables (QRS Score, $LVAT_{max}$) are recorded at baseline and are fixed. The two post-pacing variables (change in R-wave amplitude in leads V1-V2 or its CIED EGM surrogates, QRS frontal plane axis shift or CIED-EGM surrogate axis shift) are updated in response to automatic or manually commanded changes in critical pacing control parameters.

Figure 12:
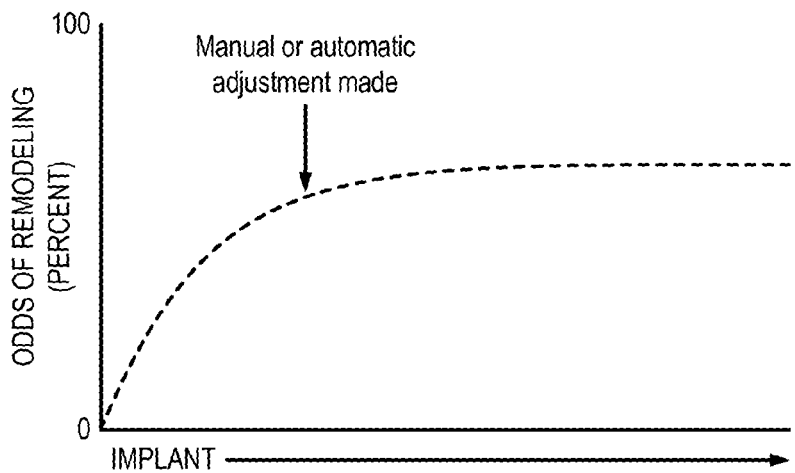
FIG. 12 is a pictorial illustration of an exemplary visual report of a probability of reverse ventricular remodeling.

The regression formula in Eqns. (7)-(8) automatically generates the odds of remodeling based on the four variables displayed. This numerical estimate is displayed on the report and automatically updated in real-time whenever the parameter variables change. This numerical output may be supplemented with a visual trending output. In this arrangement, such as the example plot illustrated in FIG. 12, the estimated odds of remodeling are displayed on the vertical axis and time (implant to follow-up, in months or years) on the horizontal axis. The dashed line is the trend of remodeling odds over time. Marker annotations are inserted at times when automatic or manual adjustments to critical pacing control parameters are made.

Figure 13:
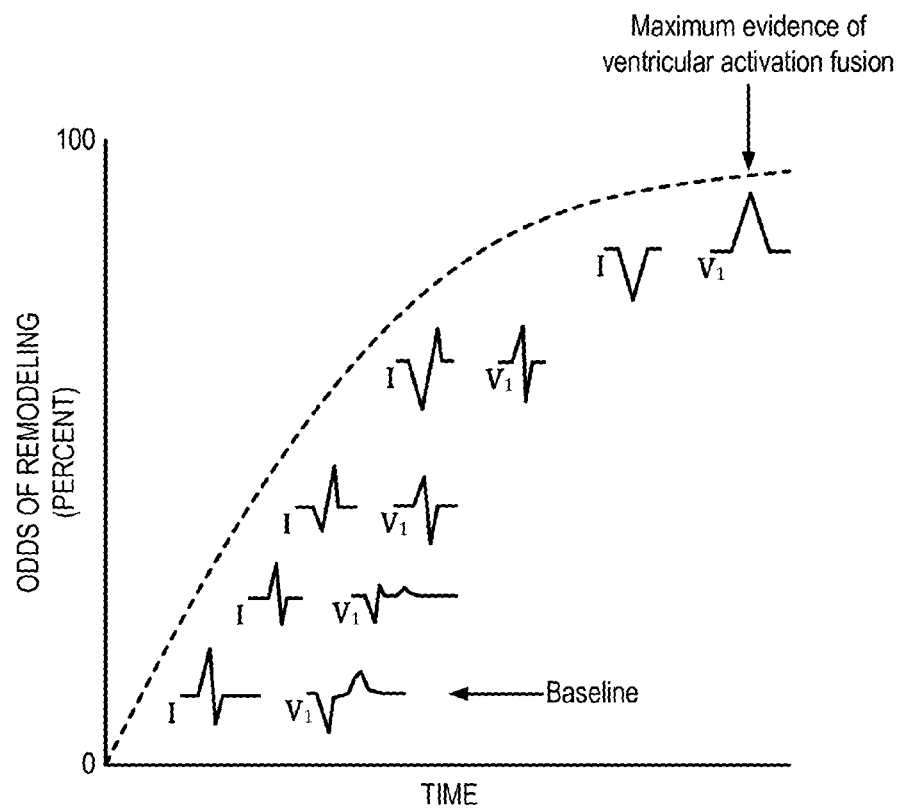
FIG. 13 is a pictorial illustration of an exemplary visual report of a probability of reverse ventricular remodeling in which QRS glyphs from a related surface ECG or CIED EGM are also displayed.
Figure 14:
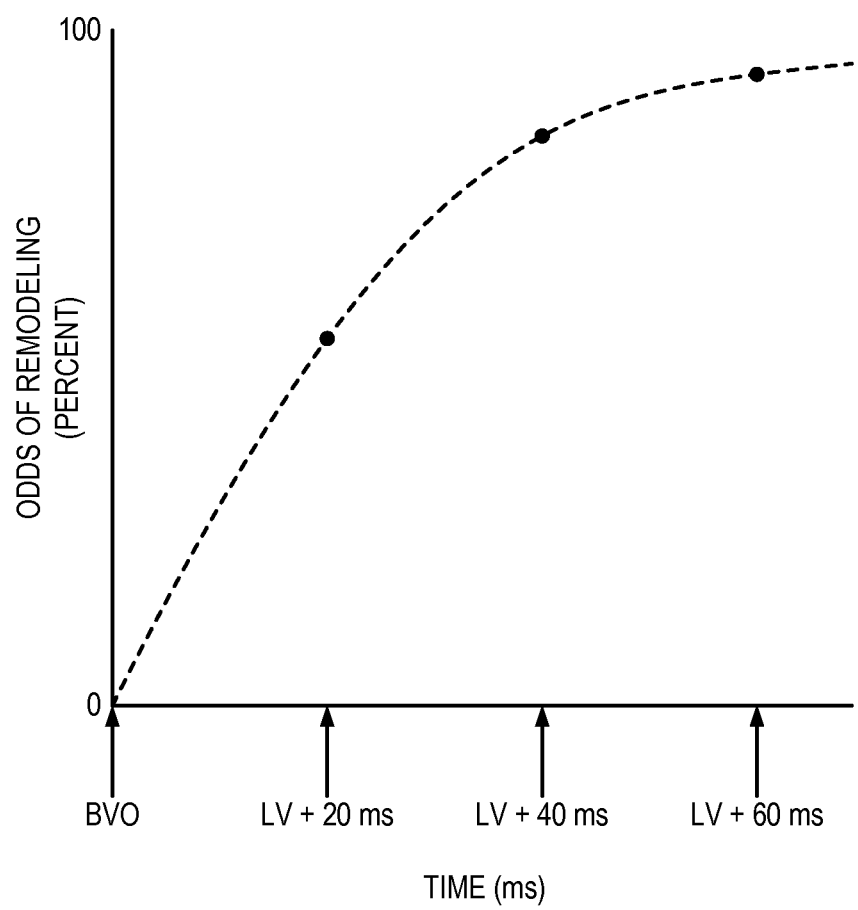
FIG. 14 is a pictorial illustration of an exemplary visual report of a probability of reverse ventricular remodeling as it is effected by changes of biventricular pacing times.

A variety of enhancements to a visual reporting arrangement for the odds of reverse remodeling are possible. For example, the trending plot could be supplemented by pivotal QRS glyphs or CIED-EGM glyph surrogates, as illustrated in FIG. 13. This would combine visual evidence of positive change in global ventricular activation with odds of reverse remodeling during manipulation of critical pacing control parameters. This arrangement could be exploited to reflect real-time changes in critical pacing control parameters. For example, in FIG. 14, a similar trending plot is used to display the "dose-response" relationship between the transition from simultaneous biventricular pacing to sequential biventricular pacing (left ventricular stimulation preceding right ventricular stimulation by 20, 40, and 60 ms). In this example, other relevant pacing control parameters such as pacemaker AVI, atrial sensitivity, and ventricular output are held constant.

Figure 15:
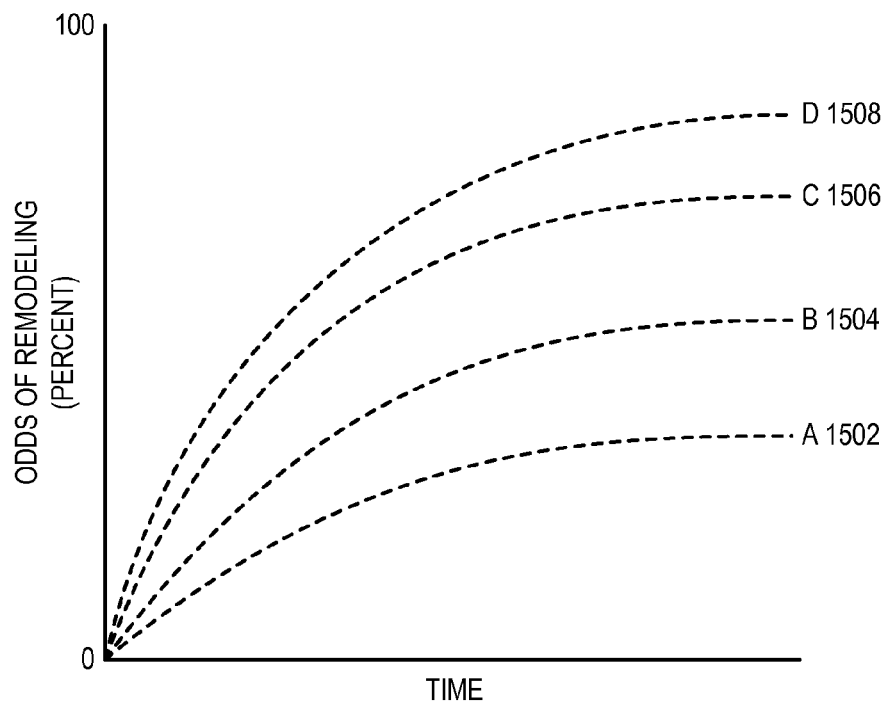
FIG. 15 is a pictorial illustration of an exemplary visual report of a probability of reverse ventricular remodeling as it is effected by changes in different pacing control parameters.

A more complex plot could be used to display the interaction between critical pacing control parameters and the dose-response relationship with odds of reverse remodeling, as illustrated in FIG. 15. Curve A 1502 displays the increasing odds of remodeling when the pacemaker AVI is held constant, for example at 100 ms, and biventricular stimulation timing is varied with progressively earlier left ventricular stimulation, for example, with 60, 40, and 20 ms left ventricular pacing delay. Curve B 1504 displays the increasing odds of remodeling when biventricular stimulation timing is held constant, such as simultaneous or sequential biventricular pacing at any value, and the pacemaker AVI is progressively shortened, which advances ventricular stimulation in both chambers and reduces conduction delay. Curve C 1506 displays the increasing odds of remodeling when both pacemaker AVI and biventricular timing parameters are adjusted simultaneously. Curve D 1508 displays the increasing odds of remodeling when left ventricular pacing output is increased, due to the "virtual electrode" effect, or change in other critical pacing control parameters such as an increase in atrial sensitivity.

Figure 16:
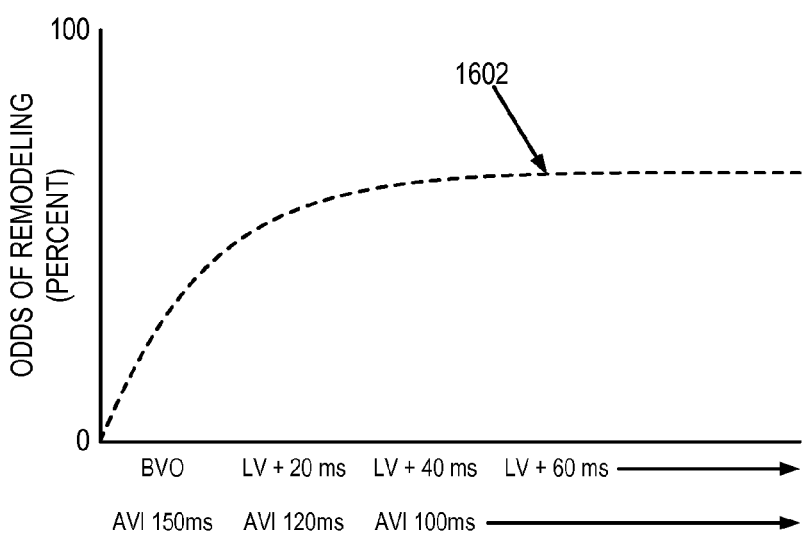
FIG. 16 is a pictorial illustration of an exemplary visual report of a probability of reverse ventricular remodeling in which a maximum probability of reverse ventricular remodeling is achieved.

Such visual displays may also be used to identify the optimal pacing control settings for maximum odds of reverse remodeling, as illustrated in FIG. 16. In this example, the maximum achievable odds of reverse remodeling occurs during sequential biventricular pacing with a left ventricular pacing delay of 40 ms and pAVI of 100 ms. Further adjustments to biventricular timing and AVI do not yield an increase in the odds of remodeling, as characterized by the plateau region 1602. Such a display may prove useful to clinicians since further unguided advancement of left ventricular stimulation or shortening of the pacemaker AVI can compromise left-sided AV timing relationships, such as atrial truncation and ventricular underfilling, resulting in reduced diastolic preload and reduction in contractility.

Thus, a system and method for integrating CIED-EGM analysis with multi-chamber electrical activation timing derived from the surface ECG in order to provide accurate estimates of left-sided atrial-ventricular timing relationships and orchestrate pacing control parameters to guarantee maximum evidence of ventricular activation wavefront fusion while reducing the risk of compromising diastolic function has been provided.

The system and method described herein for AVI management is also fully integrable with the above described system and method for automatically generating ventricular activation wavefront fusion, titrating maximum evidence of ventricular activation wavefront fusion, determining ventricular activation times, and predicting and reporting the probability of reverse ventricular remodeling. In particular, the methods for AVI management and automatically increasing atrial sensitivity work synergistically to overcome failure to achieve maximum evidence of ventricular activation fusion and reduce risk of left ventricular diastolic filling abnormalities without compromising maximal evidence of ventricular activation wavefront fusion. This approach should be particularly useful among patients with shorter PR intervals (iAVI) because pAVIs sufficiently short to generate maximum evidence of ventricular activation fusion are more likely to cause truncation of left ventricular filling (atrial transport block) when the baseline PR is short. Similarly, this combined approach should reduce the risk of left ventricular filling abnormalities under conditions of increase atrial activation time, such as atrial pacing.

The present invention has been described in terms of one or more preferred embodiments, and it should be appreciated that many equivalents, alternatives, variations, and modifications, aside from those expressly stated, are possible and within the scope of the invention.

The invention claimed is:

1. A cardiac implantable electrical device for delivering cardiac resynchronization therapy to a patient's heart, the cardiac implantable electrical device comprising:
    an input for receiving signals indicative of cardiac electrical activity in the heart;
    an impulse delivery system for delivering electrical impulses to the heart in order to provide cardiac resynchronization therapy thereto;
    a memory for storing pacing control parameters and a model of global cardiac electrical activity derived from surface electrocardiograph signals;
    a processor in communication with the memory, the processor being configured to:
        receive the received signals;
        compare the received signals with the stored model of global cardiac electrical activity that is derived from surface-lead electrocardiogram (ECG) measurements, wherein the comparison is made using a morphological framework that characterizes the received signals as surrogates for ECG measures of global cardiac electrical activity by deconstructing the ECG measures into waveform elements that are combinable into morphological patterns that are compared with the received signals;
        adjust the stored pacing control parameters based on the comparison of the received signals with the stored model of global cardiac electrical activity; and
        communicate with the impulse delivery system to provide cardiac resynchronization therapy to the heart in accordance with the received at least one of the stored pacing control parameters and adjusted pacing control parameters.

2. The cardiac implantable electrical device as recited in claim 1 in which the processor is further configured to identify one or more QRS complex glyphs in the received signals.

3. The cardiac implantable electrical device as recited in claim 2 in which the processor is further configured to compare the identified QRS complex glyphs with corresponding QRS complex glyphs in the stored model of global cardiac electrical activity.

4. The cardiac implantable electrical device as recited in claim 1 in which the processor is further configured to identify evidence of a substantially maximum ventricular resynchronization from the comparison of the received signals with the stored model of global cardiac electrical activity and bypass the adjustment of the stored pacing control parameters upon identifying a substantially maximum ventricular resynchronization.

5. The cardiac implantable electrical device as recited in claim 1 in which the processor is further configured to determine a permissible range of atrioventricular interval values from the received signals and the model of global cardiac electrical activity, and to adjust the stored pacing control parameters using the determined permissible range of atrioventricular interval values so that a probability for diastolic dysfunction is minimized.

6. The cardiac implantable electrical device as recited in claim 1 in which the processor is further in communication with the input and the processor is further configured to adjust an atrial sensitivity of the input, the atrial sensitivity being adjusted to maintain substantially synchronous ventricular activation while minimizing a probability of diastolic dysfunction.

7. The cardiac implantable electrical device as recited in claim 1 in which the model of global cardiac electrical activity is patient-specific and derived from surface-lead ECG signals acquired during a baseline and a paced condition.

8. A method for delivering cardiac resynchronization therapy to a patient's heart with a cardiac rhythm management (CRM) device, the steps of the method comprising:
 a) acquiring signals representing cardiac electrical activity in the patient's heart using electrodes in electrical communication with the CRM device;
 b) comparing the acquired cardiac electrical activity signals with a model of cardiac electrical activity that is derived from surface-lead electrocardiogram (ECG) measurements using a morphological framework that characterizes the signals acquired in step a) as surrogates for ECG measures of global cardiac electrical activity by deconstructing the ECG measures into waveform elements that are combinable into morphological patterns that are compared with the received signals; and
 c) setting one or more pacing control parameters based on the comparison between the acquired cardiac electrical activity signals and the model of cardiac electrical activity; and
 d) delivering cardiac resynchronization therapy to the patient's heart using the one or more pacing control parameters.

9. The method as recited in claim 8 in which step b) includes identifying one or more QRS complex glyphs in the acquired cardiac electrical activity signals.

10. The method as recited in claim 9 in which step b) further includes comparing the identified QRS complex glyphs with corresponding QRS complex glyphs in the model of cardiac electrical activity.

11. The method as recited in claim 10 in which steps a)-c) are repeatedly performed while continually adjusting the one or more pacing control parameters until evidence of substantially maximum ventricular resynchronization is identified.

12. The method as recited in claim 11 in which the evidence of substantially maximum ventricular resynchronization is identified in step c) by comparing the acquired cardiac electrical activity signals with the model of cardiac electrical activity.

13. The method as recited in claim 8 in which the model of cardiac electrical activity utilized in step b) includes information related to baseline global cardiac electrical activity and paced global cardiac electrical activity during ventricular activation.

14. The method as recited in claim 13 in which the model of cardiac electrical activity utilized in step b) further includes information related to global cardiac electrical activity timing metrics including ventricular activation times and atrioventricular intervals.

15. The method as recited in claim 8 in which step c) includes setting at least one of an atrioventricular interval, a ventricular-ventricular interval, and a pacing stimulus output voltage.

16. The method as recited in claim 8 in which step c) includes determining a permissible range of atrioventricular interval values and setting the one or more pacing control parameters using the determined permissible range of atrioventricular interval values so that a probability for diastolic dysfunction is minimized.

17. The method as recited in claim 8 in which the one or more pacing control parameters includes an atrial sensitivity and step c) includes setting the atrial sensitivity such that substantially synchronous ventricular activation is maintained and a probability of diastolic dysfunction if minimized.

18. The method as recited in claim 8 further comprising:
 e) calculating a probability of reverse ventricular remodeling using the model of cardiac electrical activity and the acquired signals; and
 f) producing a report indicating the probability of reverse ventricular remodeling for cardiac resynchronization therapy using the one or more pacing control parameters.

19. The method as recited in claim 18 in which step e) includes performing a regression analysis using at least a QRS score, a left ventricular activation time, a mean change in an R-wave amplitude value; and information related to a frontal place axis shift.

* * * * *